US006845657B2

(12) United States Patent
Williams

(10) Patent No.: US 6,845,657 B2
(45) Date of Patent: Jan. 25, 2005

(54) APPARATUS FOR SAMPLING DRILL HOLE CUTTINGS

(75) Inventor: Scott R. Williams, Farmington, UT (US)

(73) Assignee: Harrison R. Cooper Systems, Inc., Bountiful, UT (US)

(*) Notice: Subject to any disclaimer, the term of this patent is extended or adjusted under 35 U.S.C. 154(b) by 0 days.

(21) Appl. No.: 10/112,496

(22) Filed: Mar. 28, 2002

(65) Prior Publication Data
US 2003/0182997 A1 Oct. 2, 2003

(51) Int. Cl.$^7$ .............................. E21B 49/08; G01N 1/20
(52) U.S. Cl. ................................ 73/152.23; 73/863.21; 73/863.53; 73/863.56; 73/864.33; 175/20
(58) Field of Search ........................ 73/152.23, 863.41, 73/863.43, 863.45, 863.53, 863.56, 863.21, 863.22, 864.33; 175/20, 58, 60

(56) References Cited

U.S. PATENT DOCUMENTS

| | | | | |
|---|---|---|---|---|
| 1,606,651 A | * | 11/1926 | MacReady | 73/863.21 |
| 2,167,393 A | * | 7/1939 | Muncy | 73/864.33 X |
| 2,302,996 A | * | 11/1942 | Lilligren | 73/863.23 |
| 2,740,291 A | * | 4/1956 | Brown | 73/152.23 X |
| 2,842,965 A | * | 7/1958 | Thompson | 73/863.43 |
| 3,843,198 A | * | 10/1974 | Reynolds | 73/864.33 X |
| 3,988,243 A | * | 10/1976 | Huff | 210/297 |
| 4,332,301 A | * | 6/1982 | Jonell | 175/50 |
| 4,650,013 A | * | 3/1987 | Hoeft | 175/211 |
| 5,103,683 A | * | 4/1992 | Lyons | 73/863.51 |
| 5,894,096 A | * | 4/1999 | Kotraba et al. | 73/864.63 |
| 5,975,219 A | * | 11/1999 | Sprehe | 175/48 |
| 6,386,026 B1 | * | 5/2002 | Zamfes | 73/152.04 |

FOREIGN PATENT DOCUMENTS

| | | | | |
|---|---|---|---|---|
| AU | 200010013 A | * | 8/2000 | E21B/49/08 |
| WO | WO 98/28517 A1 | * | 7/1998 | E21B/21/06 |
| WO | WO 99/51582 A1 | * | 10/1999 | E21B/33/08 |

OTHER PUBLICATIONS

Derwent–ACGNS, 1998–521701 abstract of ZA 9711151 A, Inventor clur "Apparatus for sampling drill cuttings from drill hole in flow of air separates drill cuttings from air, directs some separated drill cuttings to collection point, samples operates automatically in response to depth of drill . . . ", Aug. 1998.*

Derwent–ACC–No: 2002–529438 abstract of AU 200235593 A, inv. Clur "Automatic drill cuttings sampling apparatus of cuttings entrained in flushing air flowing from drill hole for determination of rock structure and are grade", Jun. 2002.*

(List continued on next page.)

Primary Examiner—Thomas P. Noland
(74) Attorney, Agent, or Firm—Mallinckrodt & Mallinckrodt

(57) ABSTRACT

A sample collection device for collecting a sample of drill cuttings from a hole being drilled as the hole is being drilled includes a stem collector surrounding the drill pipe. Pressurized air is injected through the drill pipe into the hole being drilled. The air forms a stream of air-entrained drill cuttings traveling up the drill hole during drilling. This stream of air-entrained drill cuttings is directed by the stem collector into a conduit which directs the stream of cuttings to a sampling device. The sampling device samples the stream of cuttings and creates a stream of sample cuttings which is directed to a diffuser which separates the sample cuttings from the air stream. The sample cuttings are collected in a sample container or in a sample collector from which they are transferred to a sample container or bag. The stem collector seals against the ground surrounding the hole being drilled to direct substantially all drill cuttings from the hole to the sampling device, thus substantially eliminating loss of fines prior to sampling, and the sampler is designed to collect a substantially representative sample from the cuttings stream, again substantially without loss of fines and in a device which can be mounted under the drill deck of a drilling rig.

24 Claims, 19 Drawing Sheets

Figure 1:
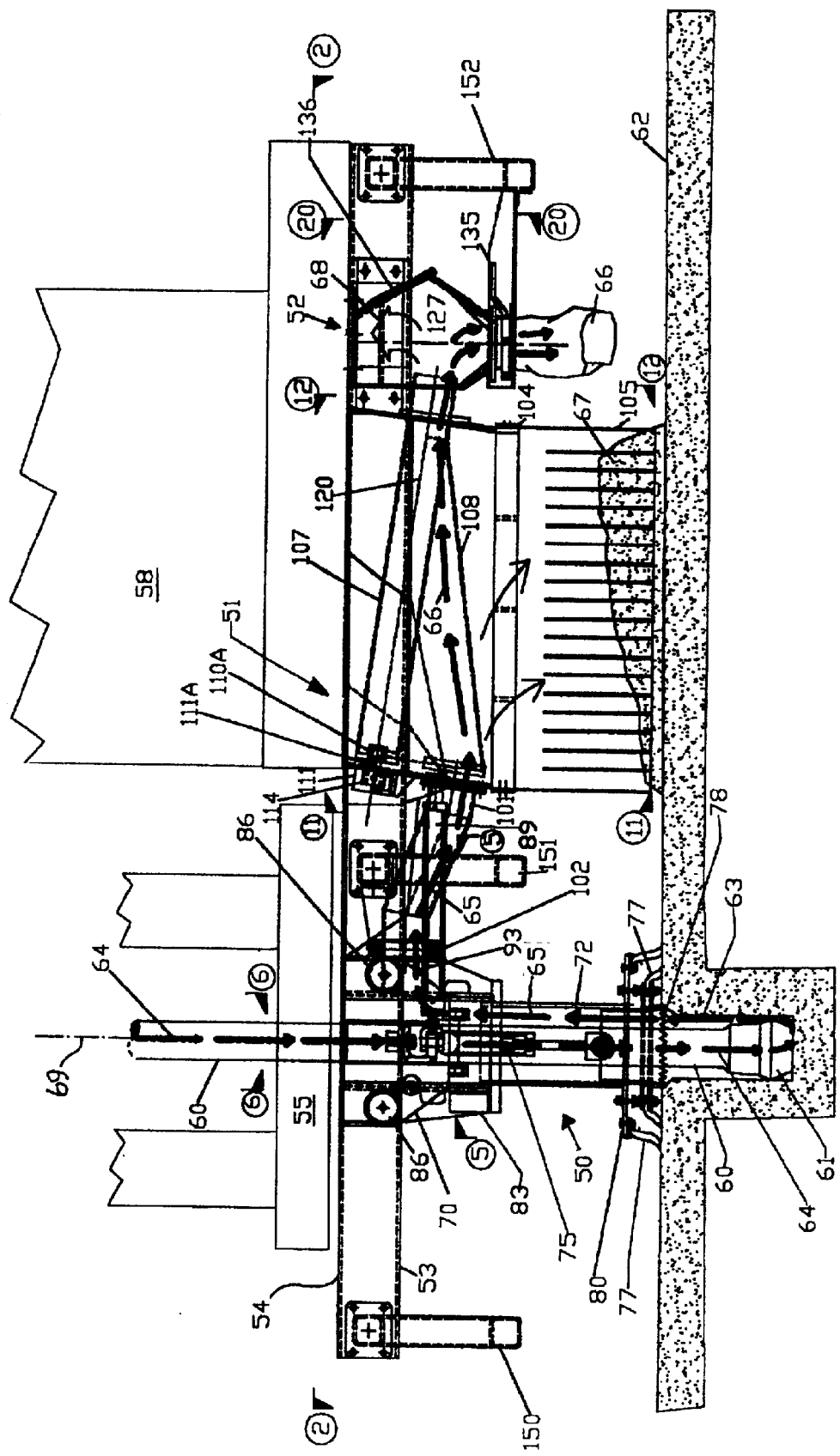

OTHER PUBLICATIONS http://www.washingtonrotating.com/products.html, download Washington Rotating Control Heads, Inc.—Product Index, 1 page, May 22, 2003.* http://www.Washingtonrotating.com/divestech.html, downloaded "The Divertech Pheumatic Diverter System" by Washington Rotating Control Heads, Inc. 4 pages, May 22, 2003.*

Harrison Cooper and Stephen Pack, "Sampling Error in Blast Hole Drilling and What Can Be Done To Improve Sample Quality," Proceedings of Sampling and Testing Symposium, Metallurgical Society and Society of Economic Geologists, San Diego Annual Meeting Mar. 1999.

* cited by examiner

APPARATUS FOR SAMPLING DRILL HOLE CUTTINGS

BACKGROUND OF THE INVENTION

1. Field

The invention is in the field of blast and drill hole sampling.

2. State of Art

During the drilling of blast holes in an open pit mine (or similarly during drilling in connection with mineral deposit exploration) the drill employs a rotary or impact (hammer) technique in penetrating underground from the surface. Material in the drill hole shatters from the drill action into small pieces with particle size typically ranging in a continuous distribution from as large as one-inch size through dust size fines. Compressed air is introduced through the hollow center of the drill pipe to transport the shattered rock (termed cuttings or drill hole cuttings) from the bottom of the hole to the surface. When applied to drilling blast-holes, composition data of material sampled during this process is used for mine production planning. Sampling can be done during removal of cuttings from the drill hole, or, alternatively, from an accumulation of drill cuttings after drilling is completed. Sampling of the cuttings from blast holes has the objective of obtaining a quantity of drilled out material suitably representative of the total volume and particle size distribution of drill cuttings removed. This is necessary so that the composition analysis carried out on the sample will be of appropriate statistical accuracy. With composition data from drill hole samples, planning of production from the mine can be developed to optimize selection of ore material to be processed and waste (non ore) material to be dumped. Efficient execution of mine production is greatly dependent on precision and accuracy of composition data used in mine planning and actual execution of each mining bench. Thus, accurate sampling is important because the sample collected is analyzed for composition.

Current sampling techniques, both those that extract the sample from the stream of drill cuttings during the course of drilling such as with a fixed sample cutter in the stream of cuttings and those that extract the sample after completion of drilling from accumulations of cuttings, cannot assure that a sample taken for analysis is representative of all the material removed from the hole-fines and coarse alike. The desired result is diminished because of size classification effects and loss of fines. This is particularly the case where the sample is taken from a pile of cuttings after drilling because fines are not retained in a static collection of material in a pile or are not distributed uniformly in the pile to be sampled due to windy conditions or other causes of size classification.

Methods used in the past to obtain suitably precise and accurate samples representing blast hole cuttings are recognized as being deficient in providing suitable data for efficient mine production planning or involve sufficient human labor to be considered economically prohibitive. The majority of past methods are generally considered to be statistically invalid. The critical requirement is reliable transfer of cuttings from blast hole drilling into a container where an appropriate reduction procedure has been applied to derive a practical size sample for testing. During the transfer process, only a minimal quantity of representative material from the drill hole should be lost. Losses are typically from the finest portion (dust) contained in drilled out material. Fines subject to loss during sample collection can be as much as twenty per cent (or sometimes greater) of material mass removed from the hole during drilling. Fines typically are substantially different in elemental composition from average material composition of the hole due to selective mineral fractionation during drill action. Therefore, separation and loss of fines potentially introduces significant bias in test results when the proportion of fines taken into the sample differs from the proportion of fines occurring in the drilled out material mass produced during excavation of the drill hole.

Drill hole material sampling should have as its objective minimizing loss of fines from the mass during sampling to assure essentially all fines particles are included in the sample for testing at about the same proportion as fines are present in the mass of material produced during drilling. However, completely representative sampling is unlikely to be accomplished in practice as some degree of fines loss will be experienced under practical operating conditions in carrying out a sample extraction procedure. A practical standard for sampling is to maintain loss offices to less than one percent of the drill hole mass as a reasonably allowed quantity so as to maintain accuracy of sampling results at an acceptable level. The objective of one percent allowable fines loss for a particular application of drill hole sampling may be adjusted to a greater or lesser value according to metallurgical and geophysical characteristics of the ore deposit being sampled. The quantity of sample extracted from drill hole cuttings to implement an efficient system of mine planning is entirely dependent upon metallurgical and geophysical properties of the ore deposit. Calculations of the quantity of sample reserved for testing is performed according to generally accepted practice. The concept may be illustrated by an example, which could be considered typical, where weight of material removed from the earth during a blast hole drilling operation is 500 kg. Based on physical properties of the ore body, a primary sample weight of five per cent, or 25 kg., is to be extracted by means of a primary sampling device. Maximum particle size from drilling is in the range of 25 mm. This quantity, 25 kg., requires reduction in weight, to about 5 kg. in typical cases, for presentation to the laboratory for composition analysis. Maximum particle size is of necessity to be reduced by crushing and grinding to a lesser value, perhaps 5 mm., to maintain sample representation validity in carrying out reduction with a secondary sampler. The final stage of reduction can be carried out in the field with an automatic second-stage reduction system installed with the primary sampler and collection system at the drill rig, or an entire 25 kg. primary sample mass can be transported to the laboratory for reduction. The sample handling procedure is selected according to specific circumstances of the mine operation.

SUMMARY OF INVENTION

The invention includes three principle parts: (1) a stem collector, usually a telescoping stem collector, mounted on the drill rig designed to seal against the ground and around the drill pipe to minimize loss offices materials to the practical degree needed; (2) a primary sampling device installed on the drill rig in conjunction with the stem collector to extract the appropriate quantity of primary sample from an air-entrained continuously flowing stream of drill hole cuttings during the course of drilling; and (3) a diffuser attached to the primary sampling device to accumulate extracted sample increments by gravity deposition in a collection container while venting pressurized air from the sampler in a manner to minimize escape of fines through the venting openings in the unit.

The mass of drilled-out material from the hole is carried up from the drill hole as drilling progresses by entraining the material in flow of compressed air injected into the hole through the center of a tubular steel drill pipe simultaneously with drilling. Air flow carries drill cuttings by entrainment transport through the top of the drill hole at terrain surface where a hollow stem collector body is provided with an outlet pipe leading to the primary sampling device to enable extracting representative sample increments of drill cuttings having proportional content sufficient for practical purposes. The drilling machine drill pipe rotates through a dust seal above or in the upper portion of the stem collector body. The stem collector is designed to minimize dust loss from escaping air through gaps where an attached base plate contacts the earth surface. The gaps are minimized by forcibly pressing the base plate and rubber seals against the earth surface. Considerable force, of 1000 pounds per square inch or more, is exerted between the bottom of the stem collector body, base plate and the ground surface. Hydraulic cylinders or electric linear drive actuators are provided to push the stem collector base plate with its sealing features against the earth surface when sample collection is to be performed to minimize fine material (dust) loss and maintain particle entrainment during the process of collection. Stem collector operation is controlled by the drill rig operator to move, raise and lower the collector as required when moving the rig to a drilling location, and for positioning the drill pipe stem through the collector body for drill operation.

The stem collector diverts mass flow from the drill hole into a pipe conduit leading to the primary sampling device which takes the form of a horizontally oriented rotary mechanical sampler. The cross sectional area of the diverting pipe is designed to maintain entrainment velocity and volume to the sampler.

There are times and conditions when the sampling system will not be used in conjunction with the blast hole drilling operation. All system components are mounted on a unitized frame which is then secured to the bottom of the drill rig frame under the operator's cab. The stem collector is equipped with wheels that allow it to be moved in a straight line along a pair of channel beams in and out of the alignment with the drill pipe when the pipe and bit have been raised above the drill deck. Part of the connecting pipe between the stem collector and primary sampling device is attached to each unit. These sections are equipped with seals and join together when the stem collector is moved into sampling position. A pair of hydraulic cylinders or electro mechanical linear actuators, remotely controlled by the drill operator, move the stem collector along the channels horizontally.

If dust produced during drilling is excessive such that dust in greater than acceptable quantities is seen escaping due to emission at the stem collector, means can be employed for dust suppression through water injection into the air entrained solids flow. Dust can be induced to agglomerate with solids by injecting nebulized water into compressed air flow at the drill stem or spraying water toward the cutting stream in the bottom of the primary sampling device enclosure. Any addition of moisture needs to be controlled so as to not exceed an appropriate level according to characteristics of the solids; otherwise, solids can become sticky due to greater than necessary water content resulting in solids adhering to walls of and possibly clogging the stem collector conduit, connecting pipe and/or primary sampling device to interfere with the sampling function. Moisture content, if water injection is needed, can be controlled to a desired level by calibrated manual practice or by providing a humidity sensor installed on a sampler reject section to indicate the moisture level in the reject cuttings.

The primary sampling device is installed on the conduit pipe from the stem collector as closely as is feasible to the stem collector. A sealing mechanical connection is provided between the stem collector and primary sampling device. This device allows the collector to be raised and then moved away from the primary sampling device without the operator being required to physically disconnect the collector and sampling device. When the stem collector is moved into position for sampling, a sealed connection is automatically achieved between the units. Proper alignment and spacing is accomplished through adjustment at the time of equipment installation on the unitized channel framework at the factory.

The principle of sampling employed by the primary sampling device for a typical design is constant speed rotary traversing motion where the sample cutter swings through the air entrained cutting stream at a maximum rotation rate (18 inches per second at a point near the midpoint of the cutter body) to maintain standards of proper extraction. In a preferred embodiment of the invention, a typical rotation rate of about fifteen to twenty revolutions per minute is appropriate with a cutter mid-point radius of six inches (150 mm). A cutter with sharpened edge blades and integral discharge pipe is attached to a mechanical drive, usually an electric motor or hydraulic rotary actuator, and as the cutter moves through the flowing air-entrained solids stream an increment of sample is removed from the stream. The sampling validity of the rotating type sampler is maintained while providing for maximum ground clearance by limiting the cutter rotation to about 180 degrees from side to side.

After rotating through the entrained cutting stream, the cutter is stopped in a near parallel position to the ground surface at least 300 mm away from the inlet opening in the sampling device enclosure. The cutter remains parked in this position until an automatic control timer signals the rotary actuator to move the cutter back through the cutting stream to park on the opposite side of the inlet opening. This timed sampling interval allows samples of different quantities and statistical volume to be taken as desired by the mine operator or dictated by metallurgical analysis of the ore body. This sample is discharged to a diffuser sample collector as previously described. The collector or collection chamber is positioned at the bottom of the diffuser. Samples are carried to the diffuser through the outlet pipe which is a continuation of the cutter body. The cutter blades are arranged radially from the center point of rotation. The cutter opening at the mid-point where the cutter intersects the sample flow is a minimum of 2.5 times maximum particle size, or approximately 62.5 mm. for maximum particle size of nominal 25 mm. Typically, length of the cutter blades is twice the diameter of the conduit bringing drill hole cuttings to the sampler. The sample cutter body and outlet pipe form a conduit to direct entrained sample toward the sample chute to the container. The outlet pipe passes through the end of the sampling device enclosure into the diffuser which helps ensure sample delivery to the collector and prevents contamination of sample from fugitive dust or other potential contaminants. Directed air nozzles located on the inlet end plate of the sampling device enclosure are positioned to blow compressed air through the cutter body and outlet pipe while in the respective parked positions on either side of the inlet to insure that all cuttings in the sample increment are blown into the diffuser sample collector. These air nozzles are automatically controlled by the sample timer through electric solenoid actuated valves.

Entrained air in the entrained sample is vented from the diffuser through vents near the top of the collection chamber.

Dust fines emission from the collector is minimized by baffles and/or filters at the top of the diffusion chamber. This results in the greatest possible proportion of dust fines for practical purposes being deposited into the compositing sample through settling by gravity into the container. When sampling stops, the cutter is stopped in a neutral park position out of the air entrained flow stream from the stem collector (the cutter is held parked out-of-stream). During the course of drilling, when the cutter is parked out-of-stream, fines are prevented from entering the cutter due to possible pressure differential between the bulk flow stream inside the sampling device enclosure and cutter body interior by a seal installed between the rotating cutter blade and the inlet end plate interior surface of the sampling device enclosure in the cutter park positions. Reject material (that is, drill hole cuttings not-extracted into the sample) is dropped to the ground by gravity directly under the sampler in a skirted enclosure.

The drilling operation typically includes "sub-drilling", or drilling deeper than the hole depth required to be blasted. Sampling is not done during drilling of sub-drill material. The sampler is turned off during sub-drilling and all cuttings are rejected into the pile under the sampling device.

THE DRAWINGS

The best mode presently contemplated for carrying out the invention in actual practice is illustrated in the accompanying drawings, in which:

FIG. 1, is a front elevation of the invention including the stem collector, primary sampling device, and diffuser sample collector showing some internal parts in broken lines and the unitized mounting framework and showing with arrows the flow of air and drill cuttings through the system during drilling operations;

FIG. 2, a top plan view of the invention and unitized framework as shown in FIG. 1 on line 2—2;

FIG. 3, an enlarged front elevation of the stem collector of FIG. 1 showing the stem collector in retracted (up) position but still in drilling alignment prior to movement away from primary sampling device with middle tubular frame brace removed for clarity;

FIG. 4, an enlarged front elevation of the stem collector showing the stem collector in retracted (up) position as in FIG. 3, but moved horizontally away from sampling device out of drilling alignment;

FIG. 5, an enlarged front elevation of the stem collector of FIG. 3 showing the stem collector extended (down) to ground surface in drilling alignment and in contact with the sampling device inlet pipe as shown on line 5—5 of FIG. 1;

FIG. 6, a vertical section of a passive stem seal to be installed above the drill deck on top of a drill deck bushing around the drill pipe as taken along line 6—6 of FIG. 1;

FIG. 7, a vertical section of the stem collector of FIG. 4 and drill deck seal assembly with stem collector moved out of the drilling alignment and frame components removed for clarity;

FIG. 8, a fragmentary top plan view of the top portion of the stem collector of FIG. 7 on line 8—8 of FIG. 7, showing the deck seal assembly installed and stem collector moved out of drilling alignment, and with unitized frame components removed for clarity;

FIG. 9, a simplified fragmentary top view similar to FIG. 8 without deck seal installed, showing the discharge conduit for drill cuttings from the stem collector separated as will happen as the stem collector is moved from its aligned position by the hydraulic cylinders as shown in FIG. 4 to the position away from drilling alignment;

FIG. 10, an enlarged vertical section of the ground seal portion of the stem collector prior to contacting the ground surface and forming a seal;

FIG. 11, a vertical elevation of the inlet end of the primary sampling device taken on the line 11—11 of FIG. 1;

FIG. 12, a vertical elevation of the outlet end of the primary sampling device taken on the line 12—12 of FIG. 1;

FIG. 13, details of the unitized frame work of FIGS. 1 & 2;

FIG. 14, a side elevation of the sampling device of FIG. 1;

FIG. 15, an enlarged top plan view of primary sampling device as shown in FIG. 2;

FIG. 16, a vertical section of the cutter assembly as shown in FIG. 14 removed from the sampling device enclosure;

FIG. 17, a cross section of inlet end of the cutter assembly of FIG. 16 taken on line 17—17:

FIG. 18, a cross section of the transition between the cutter body and outlet pipe of FIG. 16 taken near the outlet end on line 18—18;

FIG. 19, detail of cutter blades taken on line 19—19 of FIG. 16:

FIG. 20, an enlarged front elevation of the diffuser sample collector as shown on right side of FIG. 1 and taken on line 20—20;

FIG. 21, an enlarged side vertical elevation of the diffuser sample collector taken on line 21—21 of FIG. 2;

FIG. 22, an enlarged top plan view of the diffuser sample collector as shown on FIG. 2 with top plate removed for clarity;

FIG. 23, an enlarged top plan view of a sliding sample bag clamp and retrieval frame on the bottom of the diffuser (diffuser detail removed) and attached to the unitized frame as shown in FIG. 2; and FIG. 24, a side elevation of the sliding sample bag clamp and retrieval frame on the bottom of the diffuser attached to the unitized frame as shown on FIG. 1.

DETAILED DESCRIPTION OF THE ILLUSTRATED EMBODIMENT

The invention generally includes a stem collector portion 50, FIG. 1, a sampling device portion 51, and a sample diffuser sample collector section 52.

The components of the invention are mounted in a unitized steel framework 53, FIG. 1. The unitized frame of the invention will generally be secured to a moveable drilling rig used in a mine to drill blast holes into the ground into which explosive is placed to break up rock in the mine. The sample is taken from the drill cuttings obtained during drilling of the blast hole. The drilling rig includes a drill deck 55, mounted on crawler tracks for self-propelled movement of the drill rig from place to place, and hydraulic jacks with large pads which are lowered to support, stabilize and level the drill rig during drilling. The drill deck 55 supports various other components of the drilling rig such as a cab 58 for the drilling rig operator, the mast which can be raised for drilling and lowered for long moves, air compressor, and various motors and hydraulic pumps for powering the tracks for movement, rotating, raising and lowering the drill pipe and bit and performing all other necessary functions. These components are well known in the drilling industry and drilling rigs are commercially available from manufacturers such as Ingersoll Rand with an Ingersoll Rand Model DML Rotary Drill being an example.

After the drill rig is moved to the mining bench and is in position to drill a blast hole, jack supports are extended to level the machine and a drill pipe 60 with drill bit 61 at the end thereof is lowered along the drilling alignment 69 to the surface of the ground 62. The drill pipe 60 and bit 61 are rotated while being forced downward. Rotary or percussion drill bits 61 are used to break and penetrate the rock and advance the hole into the ground 62. The drill pipe 60 is generally hollow and air is forced down the drill pipe as shown by arrows 64. The air is forced into the hole 63 being drilled, generally through or around drill bit 61, and flows up the hole 63 as shown by arrows 65. As the air flows into and up the hole 63, it entrains the drill cuttings therein and carries them to the surface. Thus, the arrows 65 indicate a stream of drill cuttings, i.e., the drill cuttings formed while drilling the hole entrained in a stream of flowing air under pressure. Normally, the drill cuttings will leave the hole, fall by gravity from the entraining air, and form piles on the ground 62 around the drill hole 63. Fines usually are carried away, at least to some extent, as dust by the escaping air because they do not immediately drop out of the entraining air as do the heavier particles. Sometimes a stem collector is placed around the drill pipe as it enters the ground to direct to some extent the drill cuttings and entraining air as they escape from the hole.

Figure 10:
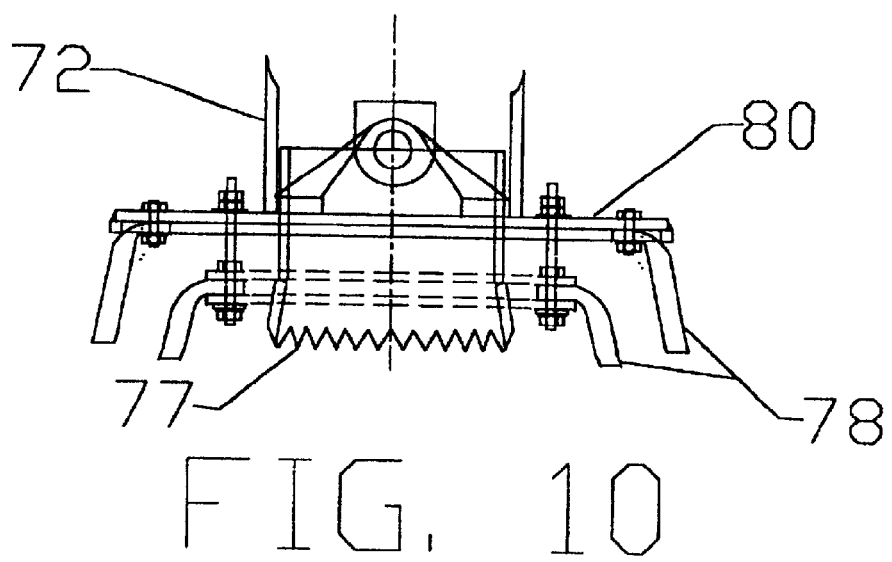

The current invention provides a stem collector 50 that surrounds and substantially seals the area around the drill pipe between the bottom of the drill deck 55 and the ground 62 surrounding the top of the hole 63 being drilled. The stem collector includes a main body 70 and telescoping base section 72. Base section 72 telescopes into main body 70 when it is retracted upward. During drilling, stem collector 50 is positioned as shown in FIG. 1, with base section 72 extended from main body 70 by telescoping hydraulic cylinders 75 on opposite sides thereof. Resilient sealing rings 77 (two tires cut to form dome-shapes a few inches apart in the current version) provide the bottom seal with the ground surface. One ring is directly attached to the baseplate 80 and the other is bolted to toothed section 78 which is positioned at the bottom of the end of base section 72 and slides inside of 72 when pressure is applied against plate 80 by cylinders 75 that forces the teeth of toothed section 78 into the ground surface 62, FIGS. 1, 5 and 10. As most clearly shown in FIGS. 1, 5, and 10, resilient inner ring 77 is secured to a base plate 80 and toothed section 78 using bolts that allow some upward movement for sealing purposes. Base plate 80 is secured to base section 72 by a continuous weld. As inner resilient ring 77 is pressed against ground 62, FIG. 1, it compresses pushing toothed section 78 upward until the physical limit of upward travel is reached and teeth 78 bite into the ground surface while resilient ring 77 flattens around the hole forming a seal. The telescoping hydraulic cylinders 75 provide one thousand pounds per square inch or more downward force on the base plate 80 during drilling operations. As base section 72 is retracted from the ground surface and ring 77 raises above the surface, toothed ring 78 is allowed to hang loosely from base plate 80 by the bolts connecting them.

Telescoping hydraulic cylinders 75 preferably provide the pushing force on the stem collector 50, however, 24VDC, one thousand pound linear actuators can be used. Telescoping hydraulic cylinders 75 are attached to main body 70 with trunion mount and base plate 80 using bolt through swivel rod end through matching bracket welded to the base plate 80. Hydraulic hoses or stainless steel lines extend from the cylinders to a control valve manifold. The valve manifold is supplied with hydraulic fluid under one thousand pounds per square inch pressure via a hydraulic supply hose from a hydraulic pump and regulator valve mounted integral to the drill rig. Fluid is returned to the drill rig hydraulic reservoir via a hydraulic return hose. To extend or retract the cylinders 75 a signal is sent to the manifold from the control panel located in the cab. Hydraulic oil is directed to the cylinders 75 and the appropriate action takes place. Force against the base plate and thus the ground is regulated by pressure relief valves in line with the hydraulic cylinders 75. When the desired pressure is reached the relief valve bypasses additional hydraulic oil back to the hydraulic tank on the rig. A proximity sensor 83 is provided to indicate via a light on the control panel that the base section 72 is fully retracted upward.

The stem collector 50 is moved along the channel beams 54 of the unitized frame 53 on chain hoist trolley wheels 86 which are attached to the main body 70. There are two wheels 86 that ride against the bottom flanges of channel beam 54 on each side of the top of main body 70 and two wheels 86 against the top flange of the channels 54 spaced equally between the bottom wheels on each side of 70. The stem collector main body 70 is also equipped on each side with a cam follower wheel 87 attached by a flange on each side of the unit that rides against the outside surface of the channel beams 54 to prevent spreading and detachment of the stem collector 50 from the unitized frame 53. Horizontal movement of the stem collector 50 along the channel beams 54 is enabled by a pair of twenty four inch double acting hydraulic cylinders 89 with clevis mountings on either end. The tube of these twenty four inch cylinders 89 is attached by way of clevis mounting brackets 90 that are welded to the unitized frame 53 next to the sampling device 51. The rod end of these hydraulic cylinders 89 is attached to the main body 70 of the stem collector 50 by way of a clevis mounting bracket 91 welded to the main body 70. Hydraulic hoses connect the twenty four inch hydraulic cylinders 89 to the hydraulic control valve manifold. The valve manifold is supplied with hydraulic fluid under one thousand pounds per square inch pressure via a hydraulic supply hose from a hydraulic pump and regulator valve mounted integral to the drill rig. Fluid is returned to the drill rig hydraulic reservoir via hydraulic return hose from the valve manifold. To move the stem collector 50 into drilling alignment 69 with the drill pipe 60 or to move the stem collector 50 out of drilling alignment with drill pipe 60 when the drill pipe 60 and bit 61 are raised above the drill deck 55, the driller activates a remote switch inside the cab, sending a signal to the hydraulic control valve manifold which causes the proper valve to be opened and hydraulic oil to be delivered to the hydraulic cylinders 89 through hoses thereby causing the cylinders 89 to extend or retract.

When the stem collector 50 is in alignment with the drill pipe 60 and bit 61 there is a mated connection between the stem collector outlet pipe 93 and the sampling device inlet pipe 101. Seal 102 between outlet pipe 93 and inlet pipe 101 helps insure a good connection between the stem collector 50 and sampling device 51. Alignment between 93 and 101 is preserved by both units 50, 51 being mounted onto the same heavy framework 53.

Figure 7:
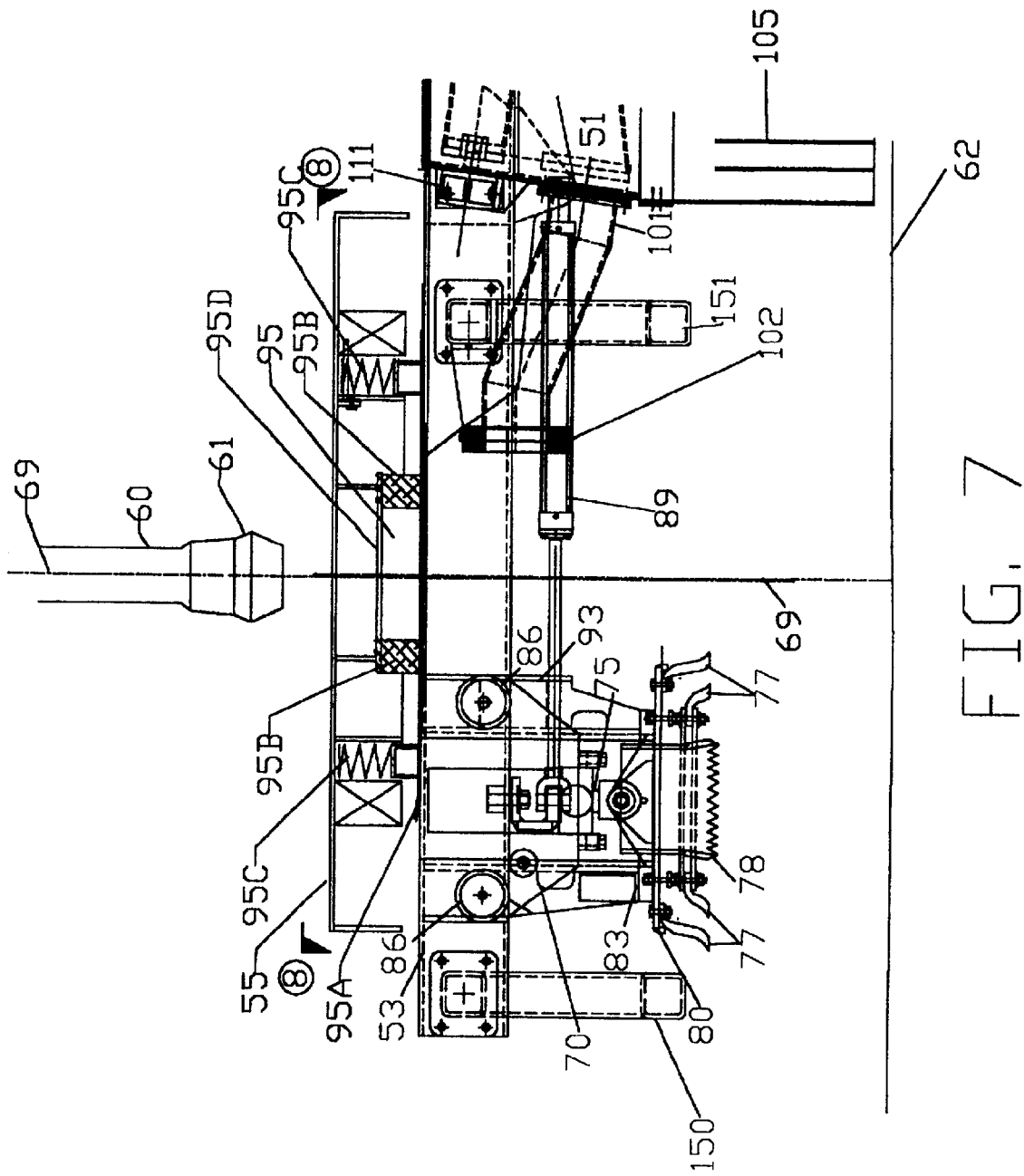
Figure 8:
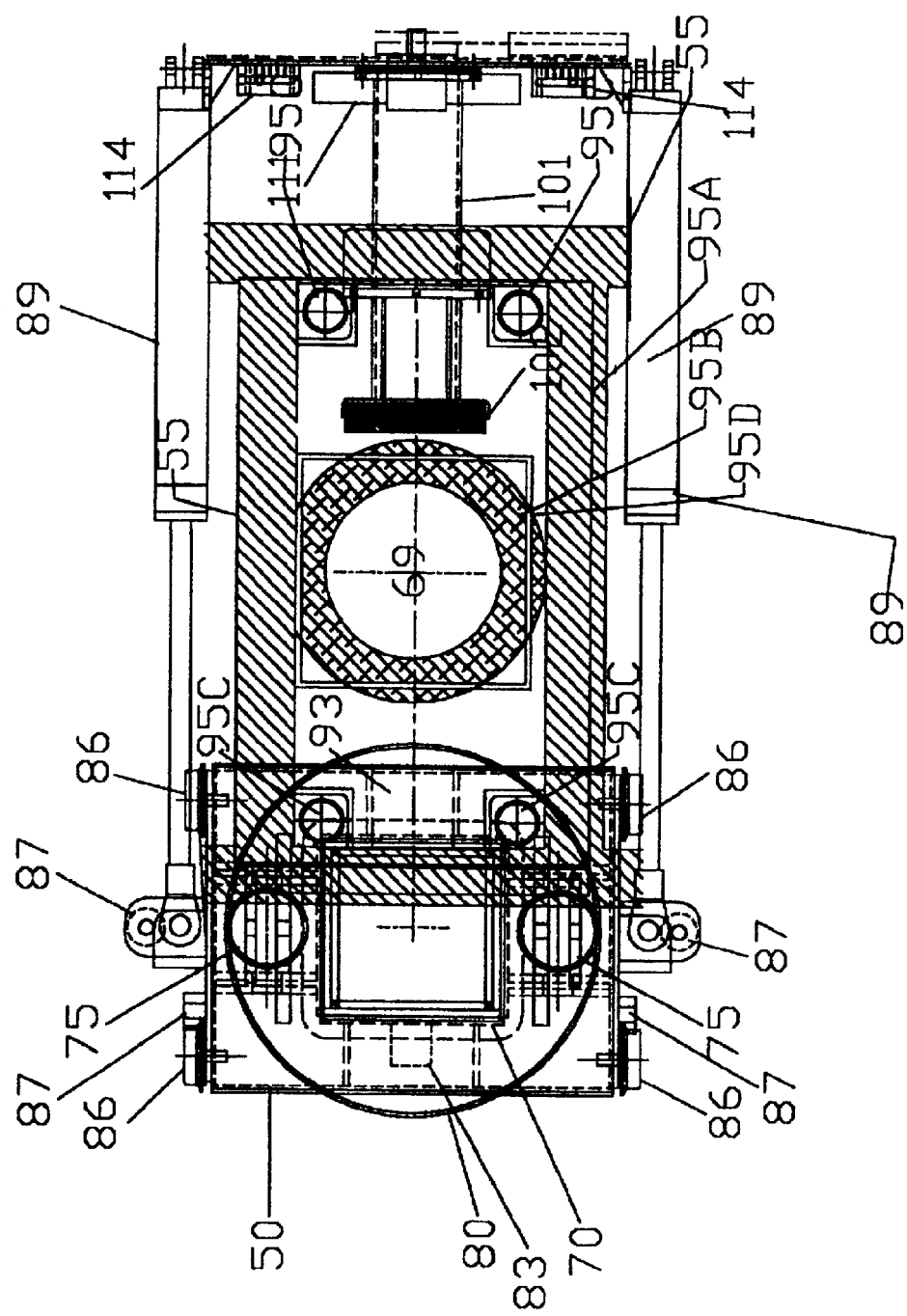
Figure 9:
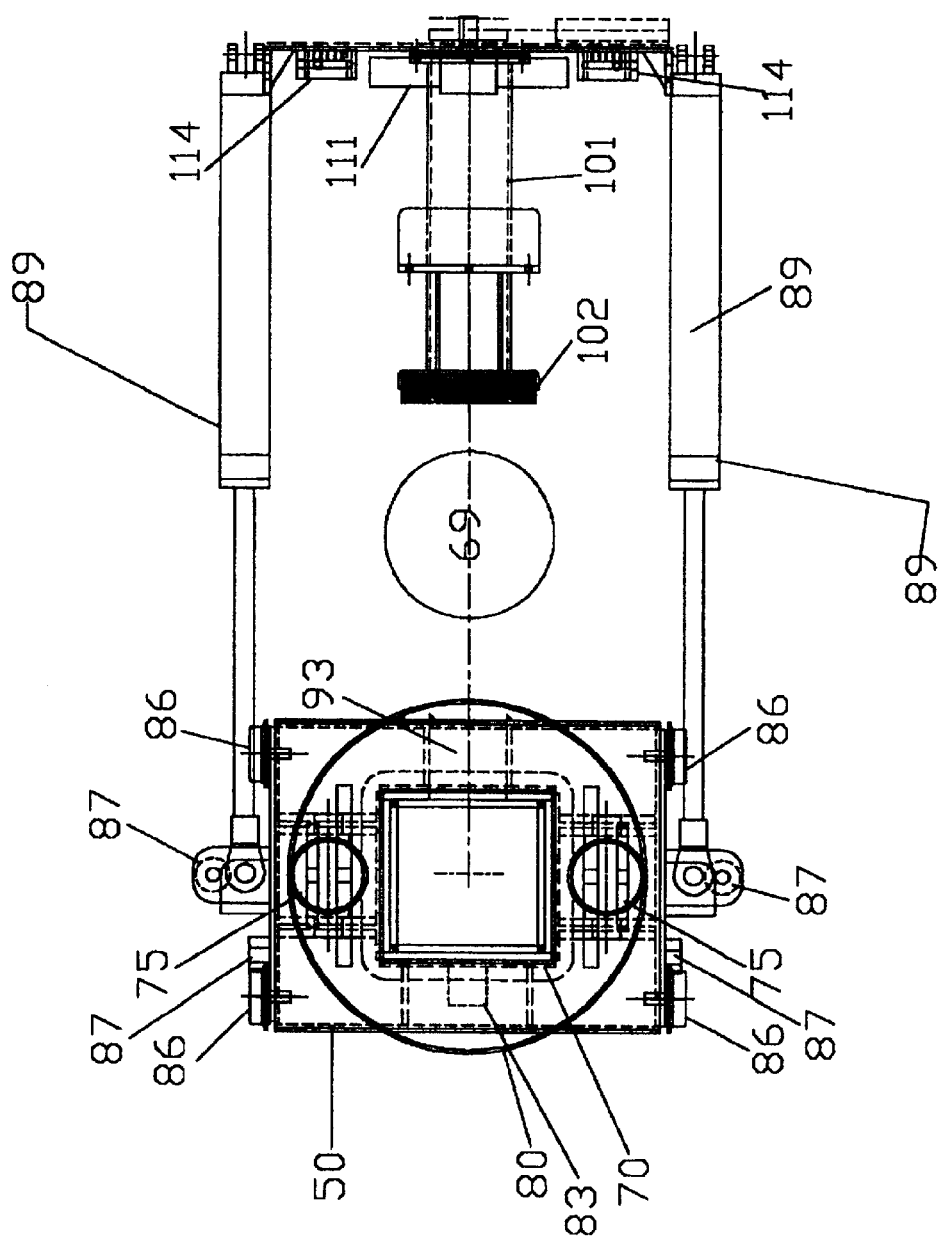

Since the stem collector 50 has no solid connection to the drill deck 55, a spring tension seal assembly 95, FIGS. 7 and 8, is provided, if needed. The assembly 95 is attached to the bottom of the drill deck 55 and is equipped with four tension springs 95D attached to a steel skid plate 95A with a thick rubber donut seal 95B and pressure plate 95C in line with the deck bushing 59 of the drill rig drill deck 55. When the stem collector is moved into drilling alignment, the top section 70 is forced against the skid plate 95A compressing the springs 95D and forcing the skid plate to squeeze the rubber donut 95B against the pressure plate 95C forming a seal between the drill deck 55 and stem collector 50. The drill string passes through the donut seal 95B. Some installations may not require this seal or may require a different assembly between 50 and 55.

Figure 6:
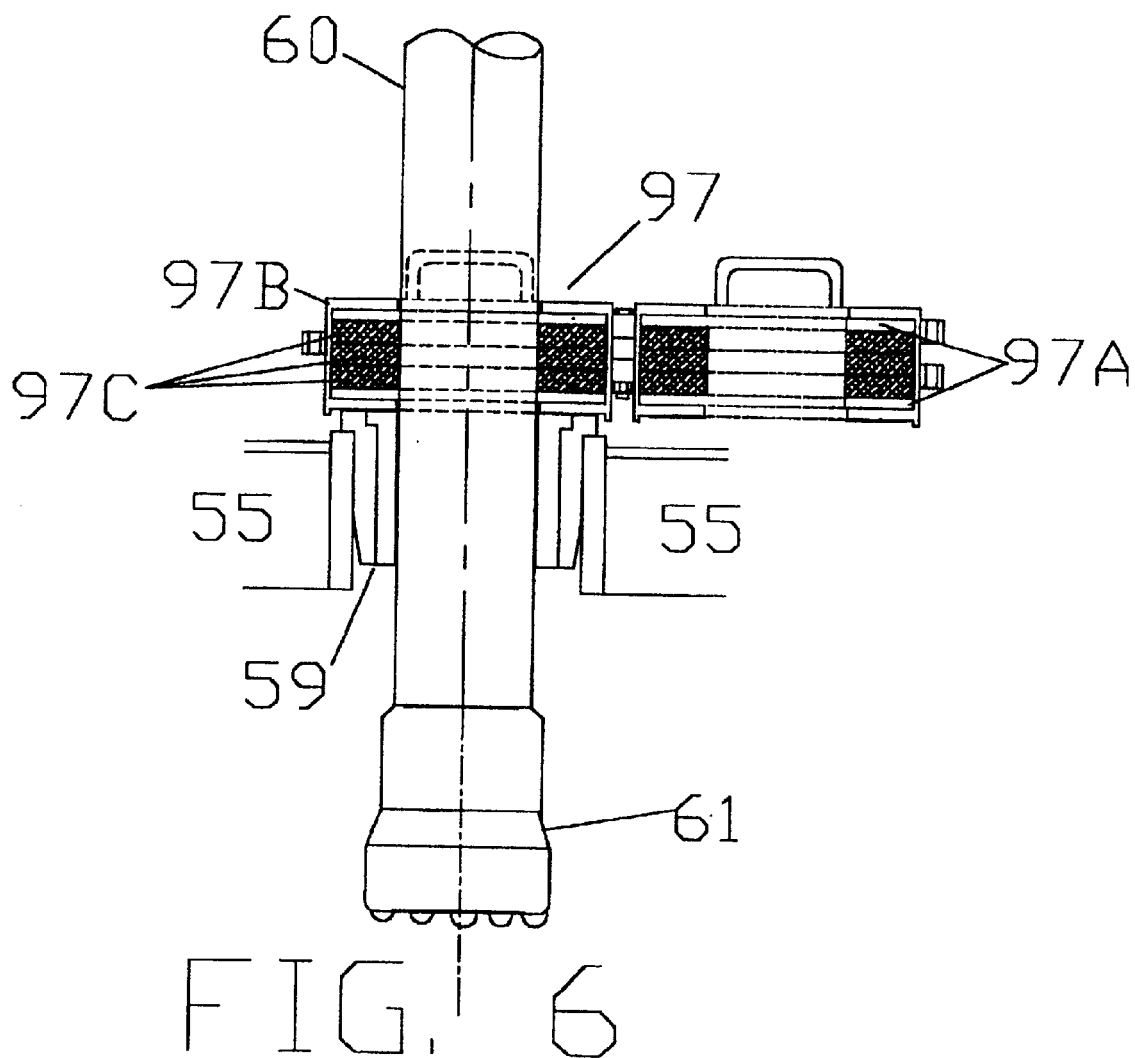

To seal around the drill pipe 60 and prevent the loss of fine cuttings (dust) which are important to sample statistical validity, a seal assembly 97, FIG. 6, is provided above the deck bushing 59. This seal 97 sits directly on the deck bushing 59 and consists of four main parts. The bottom seal section 97A is made of a high molecular weight plastic that acts like a bearing surface against the deck bushing. Above 97A is a sealing brush retainer 97B. The sealing brush 97C is made from layers of a thick highly durable abrasive pad material with a hole cut in the center to fit tightly around the pipe 60. The entire assembly is held down against the deck bushing 59 by a steel weight plate 97D. This seal system requires no attention from the driller during normal operations. When the drill pipe 60 and bit 61 are raised above the drill deck 55, the deck bushing 59 which is smaller than the bit is automatically lifted also. When the pipe 60 is lowered back into the drill hole, the bushing 59 centers it by dropping into a hole in the center of the deck 55. The seal assembly 97 slides down remaining in contact with the deck bushing 59 and the brush seal 97C remains in contact with drill pipe 60 during drilling.

The particular stem collector construction shown and described is not critical as several stem collectors have been designed for drilling with various types of seals around the drill pipe and various locations for such seals. This stem collector 50 is however unique by its integrated design into this automated system with its unitized frame 53 securing all main components for alignment and operation. The critical thing for the stem collector 50 of the invention is that the stem collector substantially seal around the drill pipe 60 and the ground 62 around the hole being drilled to reduce to an acceptable level the escape of air with entrained fines or other drill cuttings therein. It is critical for the invention that substantially all of the drill cuttings be directed from the hole to the sampling device and the stem collector serves the purpose of directing the stream of drill cuttings 65 in the entraining air from the hole to the sampling device. While the degree of loss that can be tolerated will vary with the particular purpose of the sampling, and may be determined depending upon the purpose of the sampling being done, for a good representative sample of the cuttings from the hole being drilled, it is currently preferred that the loss of fines from the hole to the sampling device be less than one percent.

Figure 3:
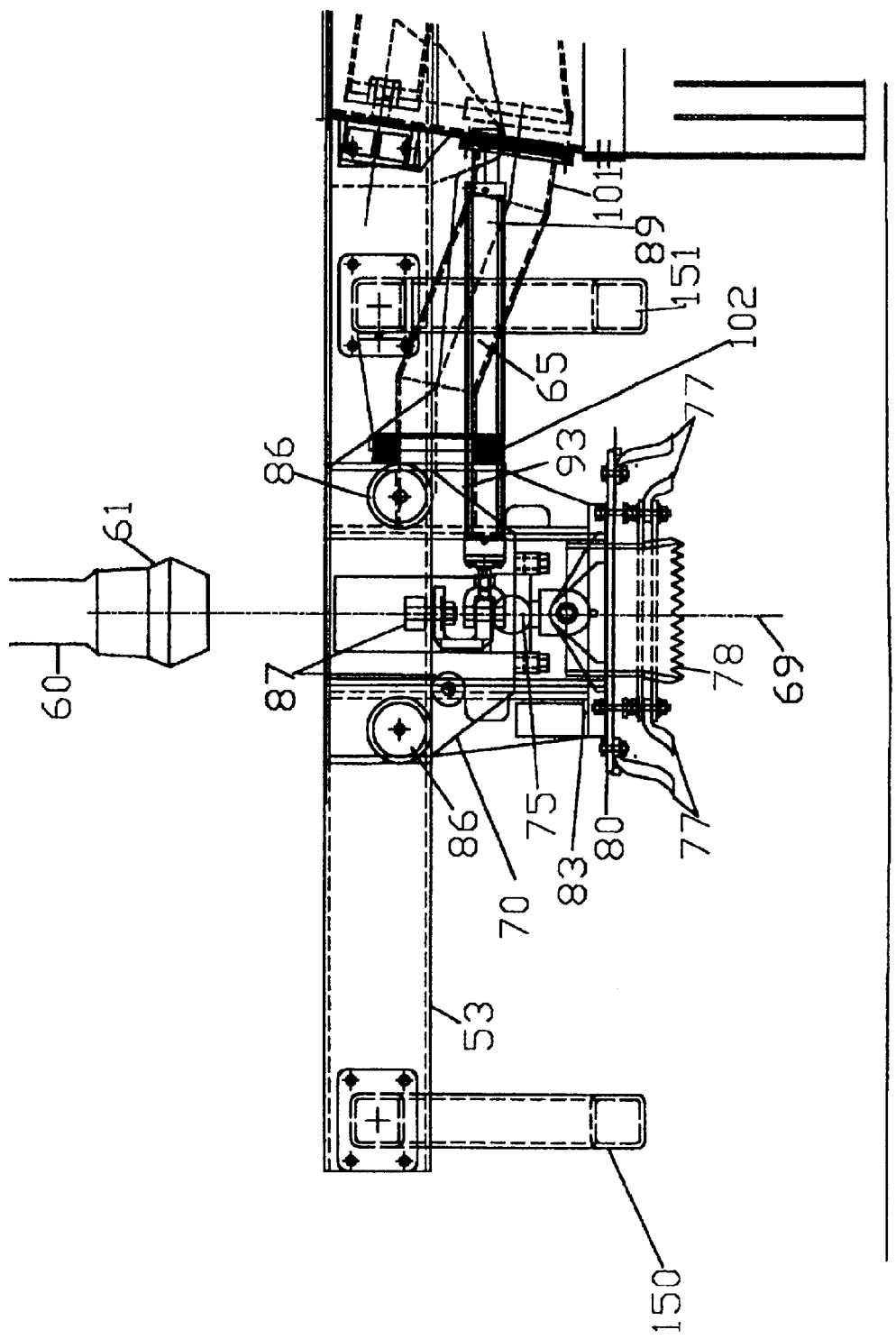
Figure 4:
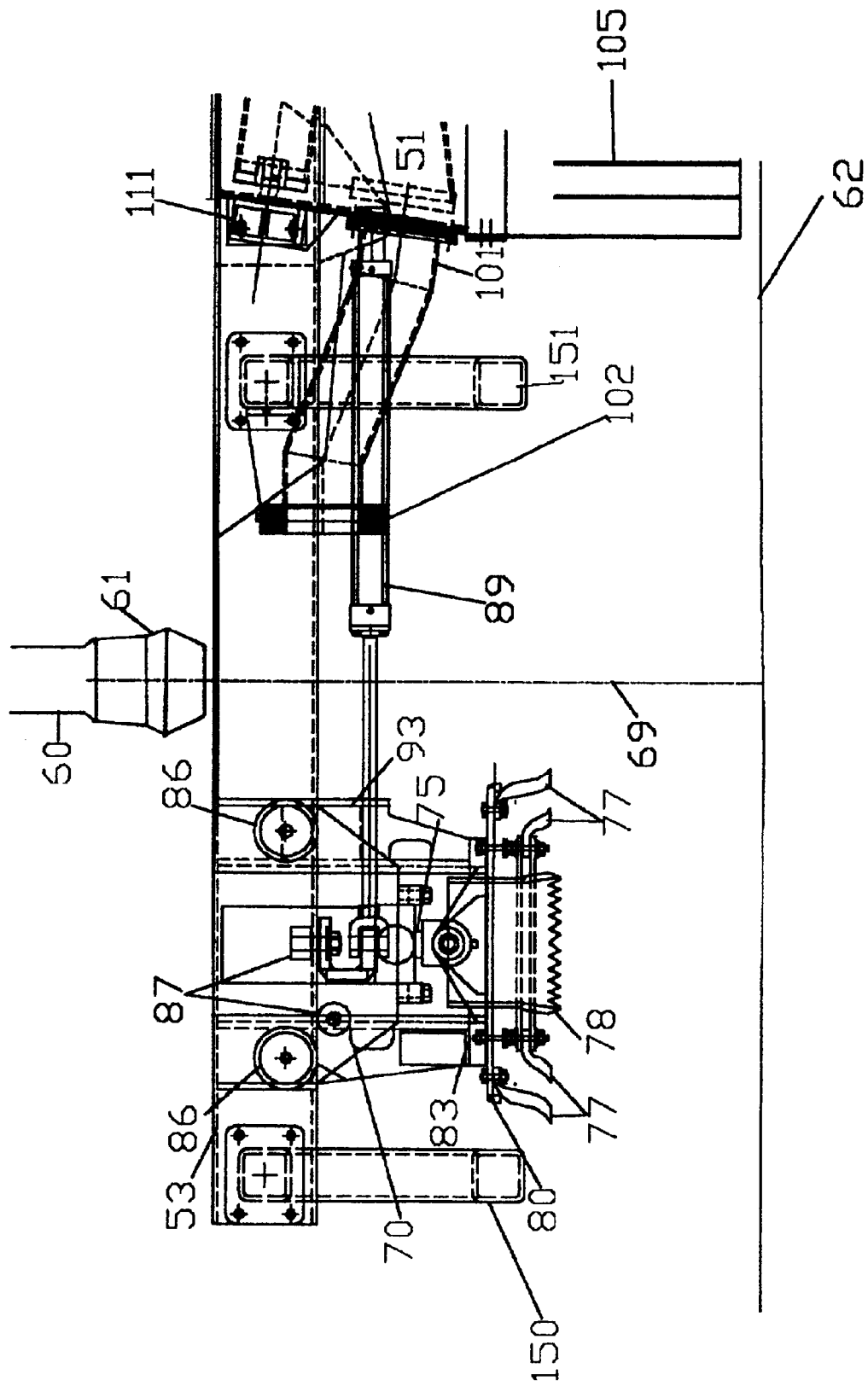
Figure 5:
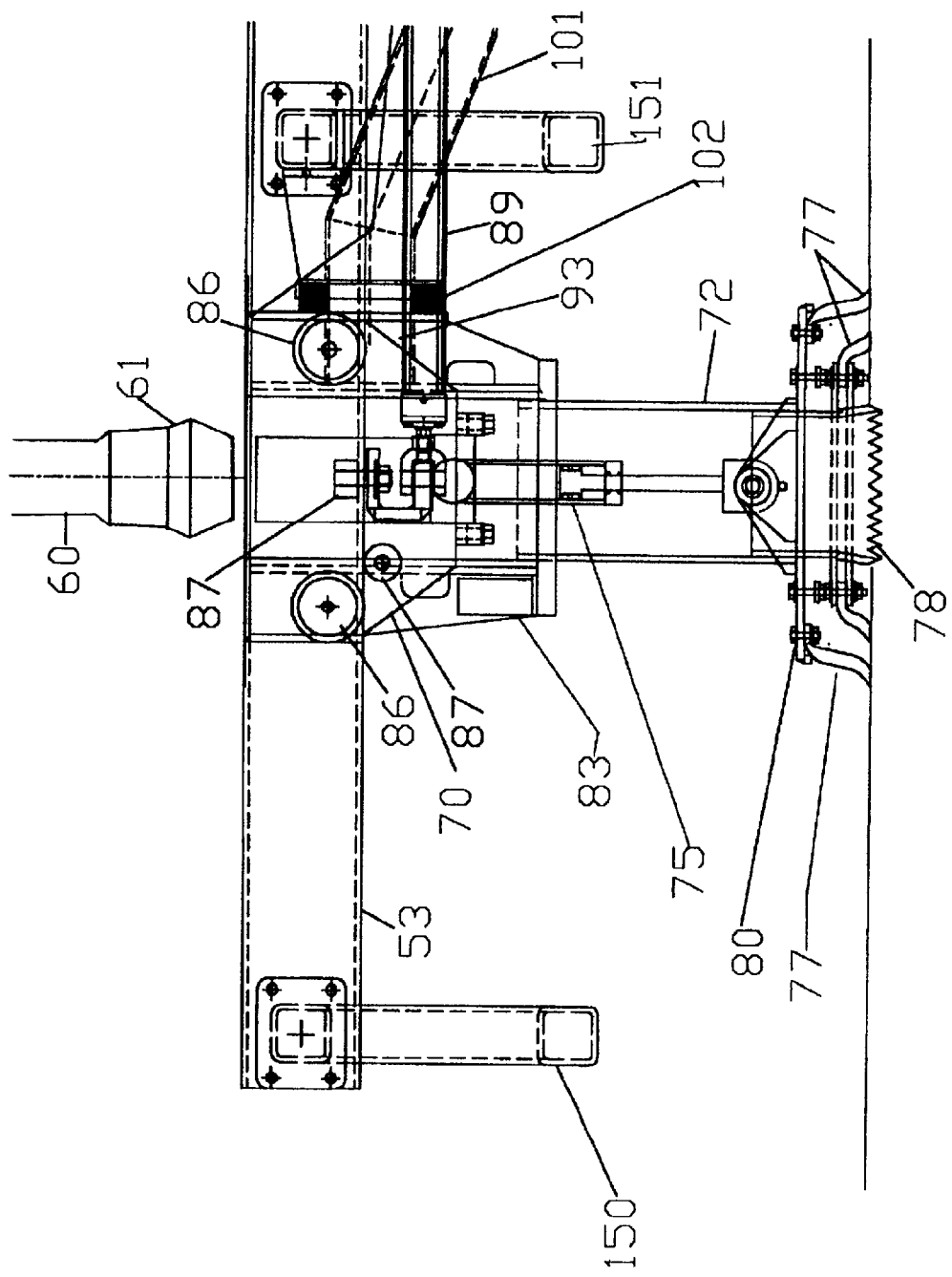

To facilitate movement of the drill rig, stem collector 50 may be retracted as shown in FIGS. 3 and 5. The rig can be moved with the stem collector 50 in either position shown. The critical factor for rig movement is the upward retraction of base section 72 into main body 70. For short moves around the mine bench, the stem collector 50 may be left in drilling alignment 69 in the up retracted position. Telescoping hydraulic cylinders 75 are operated to draw base section 72 into main body 70, FIG. 3. Double acting twenty four inch hydraulic cylinders 89 are used to move stem collector 50 into and out of alignment with drill pipe 60 and bit 61.

A stem collector outlet 93 extends from stem collector main body 70 for connection to a sampling device inlet 101. Connection from stem collector outlet 93 to sampling device inlet 101 is through a straight gasketted connection.

Drill cuttings inlet pipe 101 is welded on to the inlet end plate 100 of the sampling device 51 and provides the path for entrained cuttings 65 coming from the drill hole 63 through stem collector 50 and outlet pipe 93 to enter sampling device 51 and be sampled or rejected to the ground 62 under the sampling device 51. Sampling device 51 is a rotary cutter type sampler with its cutter 106 arranged horizontally to sample from an air-entrained cutting flow 65 rather than vertically which is the traditional orientation for using these types of samplers in a gravity flow of materials from conveyors and chutes. The horizontal arrangement of the sampling device is necessary if it is to fit under a drill deck. Otherwise, such a sampler would have to be mounted on top of the drill deck and have a means of transporting all of the cuttings to a point above the sampler. In most cases, blast hole drilling rigs do not have sufficient clear space above the drill deck to accommodate the necessary equipment and air entrainment of cuttings becomes a difficult task as the sampler gets farther away from the drill hole and gains elevation. The purpose of the sampling device 51 is to separate a representative sample of drill cuttings from the air-entrained stream of drill cuttings throughout the drilling process. To do this the stream of drill cuttings must contain substantially all of the material being removed from the hole being drilled. Then, the sampling device must reduce the amount of this material to a desired sample size that is statistically representative of the total material coming from the hole. This means that the sample must be separated from the stream of drill cuttings in a way that every particle in the cuttings stream has equal probability to be included in the sample.

The sampling device 51, as shown in FIGS. 1, 2, 11, 12, 14 and 15, includes an outer enclosure 103 which supports the sampling device components and is securely fastened to the channel beams 54 of the unitized frame 53. Cuttings inlet pipe 101 is welded to the inlet end plate 100 so that the cuttings stream 65 passes from the inlet pipe 101 into the sampling device. Enclosure 103 is open at its bottom retainer ring 104 and has skirt 105 attached to the flat bar retainer ring 104 using bolts. The skirts 105 extend downwardly toward the ground from the retainer ring 104. Skirts 105 are also open where they contact the ground surface 62. The total volume of the drill cuttings coming from the drill hole comprises both that which will be collected by the sampling device called sample 66 and the remainder of the total drilled out material called reject 67. Reject 67 exits the device through this open bottom 104 inside skirts 105 and as the entraining air expands and slows as it leaves the sampling device bottom, the cuttings entrained therein fall to the ground in a pile as shown on FIG. 1.

A sample cutter assembly 106 is made up of an outlet pipe 107, a cutter body 108 with replaceable cutter blades 109 and connecting flange 110. The cutter body 108 has a pie-shaped opening on its inlet end. The shape of the opening and its particular size and angles are determined by calculations of the desired sample as a percentage of the total volume and the position of the centerline of the inlet pipe 101 opening relative to the centerline of the outlet pipe 107. The cutter body 108 is attached to the outlet pipe 107 along its length with bolts or welds. A UHMW lining of the cutter body 108 may be provided when considerable sticky sample material is expected. A long gradual taper is maintained on the cutter body 108 to present minimal resistance to the flow of entraining air through the cutter body and outlet pipe 107. The transition from the cutter body 108 into the outlet pipe 107 is designed at a parallel angle with the outside of the cutter body to help maintain a consistent air flow. The cross sectional area also closely matches the cross sectional area of the outlet pipe to help maintain air pressure until the sample reaches the diffuser sample collector 52. The outlet end of the cutter outlet pipe 107 is supported by a machined bushing 116 made from Nylatron, UHMW or Delrin. The outlet pipe bushing is bolted to the outlet end plate 115 of the enclosure 103. The inlet end of the cutter assembly 106 is equipped with a connecting flange 110 with a female spline or keyed receiver 110A welded in the center. The flange can be welded directly to the end of the outlet pipe 107 or secured by bolts to a plate with tapped holes that is welded to the end of the pipe 107. The female receiver 110A receives a matching output shaft 111A extending through a hole in the inlet end plate 100 from a hydraulic rotary actuator 111 which is bolted to the outside of the end plate 100. The hydraulic rotary actuator provides the force to rotate the cutter assembly 106. The cutter assembly 106 is rotated through the air-entrained cutting stream in a one hundred eighty degree arc 123 between parked positions on either side 121 or 122 of the centerline 120 of the cutter outlet pipe 107 as shown on FIG. 11. As the opening into the cutter body 108 passes across the opening of the inlet pipe 101, entrained cuttings 65 under pressure are collected into the cutter and blown through the cutter body 108 to the outlet pipe 107 and on into the diffuser sample collector 52 which is attached to the channel beams 54 of the unitized frame 53 adjacent to the outlet end plate 115 of the sample cutter enclosure 103. To protect the cutter body 108 from excessive wear and provide precision definition to the limits of its opening, replaceable knife edged cutter blades 109 are bolted to the sides of the cutter body 108. Details of the cutter configuration are shown on FIGS. 16–19.

A layer of one inch thick woven abrasive material is used as a brush cutter seal 119 on the inside of the inlet end plate 100 of the enclosure 103. This material was chosen for its durability and woven characteristics. It will provide a dust resistant barrier when the cutter 106 is in the parked positions 121 and 122 to prevent any reject fines that are circulating freely inside of the enclosure 103 from migrating into the cutter body 108 and causing a sample bias thereby adversely affecting the statistical reliability of the sample collected. The brush seal 119 is glued to the inside of the inlet end plate 100 only in the area of the parked positions 121 and 122. The area of the inlet pipe 101 will not have any brush seal installed near it.

It is currently preferred to make the pie shaped cutter body 108 and cutter outlet pipe 107 and cutter blades 109 from stainless steel. To help prevent sticking of sample particles in the cutter body 108 a lining of UHMW (ultra high molecular weight plastic) is preferably used inside the cutter body 108.

Rotations of the cutter 103 are controlled by an electronic control timer. Automatic sample time intervals can be set from zero seconds which means that the cutter 103 is sampling as if it was rotating continuously at a speed of eighteen inches per second or less to one minute which equates to the cutter 106 rotating through the cutting stream 65 once every minute. Typical settings would range from five seconds to twenty five seconds depending on the quantity of sample desired or according to sampling accuracy determined for the particular conditions and ore characteristics. The timer setting in seconds represents the number of seconds that the cutter 103 remains parked at either position 121 or 122 before it is rotated through the cutting stream 65 at 101 to take the next sample. Cuttings not included in the sample collected are called reject 67, drop to the ground 62 under the sampling device enclosure 103 within the skirted area.

The preferred method of providing the rotational force to the cutter assembly 106 is the installation of a one hundred eighty degree hydraulic rotary actuator 111 on the inlet end plate 100 of the sampling device enclosure 103. The hydraulic rotary actuator 111 is bolted to the end plate 100 with its output shaft 111A extending through the end plate 100. The cutter is installed by positioning the center line of cutter body 108 in line with the center line of the inlet pipe 101 and sliding the female receiver 111B onto the splined or keyed output shaft 111A. The rotary actuator must be in its neutral position half way between the limits of its rotation which represents the midpoint between parked positions 121 and 122. After the splines or key and key way of 111A and 110B have been mated, the outlet pipe bushing 116 can be slid onto the outlet pipe and bolted to the outlet end plate 115 of the sampling device enclosure 103. Limits of rotation of the hydraulic rotary actuator 111 are determined by the limits of actuator model at one hundred eighty degrees of total travel or a ninety degree rotation on either side of the centerline of the inlet pipe 101. Activation of the actuator is accomplished by hydraulic fluid under one thousand pounds per square inch pressure being delivered via hydraulic hoses to either side of the actuator as determined by signals sent from the control timer in the cab to the 24VDC solenoids controlling the valves in the manifold The hydraulic fluid under pressure is supplied to the hydraulic control valve manifold via a hydraulic supply hose from a hydraulic pump and pressure regulator mounted integral to the drill rig. Hydraulic oil is returned to the rig hydraulic reservoir via a return hydraulic hose. Speed of rotation is set by manipulating port flow control valves integral to the rotary actuator 111. Although the use of the hydraulic rotary actuator 111 is the preferred choice for powering the cutter 103, an electric motor, such as a one-hundred ten volt single phase reversing motor, operating through gear reducer, such as a right angle helical worm reducer with an output speed of about fifteen rpm, connected with a splined or keyed output shaft could also be used to power the rotation of the cutter 106 as an alternative if desired. The electric motor alternative requires more complicated controls and accessory parts such as motor starters, limit switches and relays for operation.

To help ensure cuttings do not stick to and/or build up in the sample cutter body 108 and/or the outlet pipe 107 due to slightly sticky cuttings or loss of entrainment air from the drill hole, air jets 114 are installed through the inlet end plate 100 of the sampling device enclosure 103 at each cutter parked position 121 and 122. These air jets 114 are aimed so they direct a compressed air blast down the cutter body 108 and outlet pipe 107 from the inlet end plate 100 toward the outlet end and diffuser sample collector 52. When the cutter body 108 reaches either parked position 121 or 122 an air blast is turned on at position 121 and remains blowing until the cutter 103 is rotated toward the opposite parked position 122. When the cutter reaches position 122 an air blast is directed down the cutter body 108 through the duration of the time the cutter is parked in that position. Air is supplied to the air jets 114 via hoses through 24VDC solenoid controlled two valve manifold supplied with compressed air from an air hose connected to the drill rig compressor receiver tank. Solenoid control is provided through signals from the timer control in the drill rig cab. When the cutter reaches a parked position a signal is sent to the solenoid controlled manifold and air is directed to that jet. When the signal is sent for the cutter to be rotated toward the other parked position, the control timer sends a signal to the solenoid to open the applicable valve and close the prior path to the other jet. The jets 114 are inactive when the sampler 51 is turned off.

Figure 11:
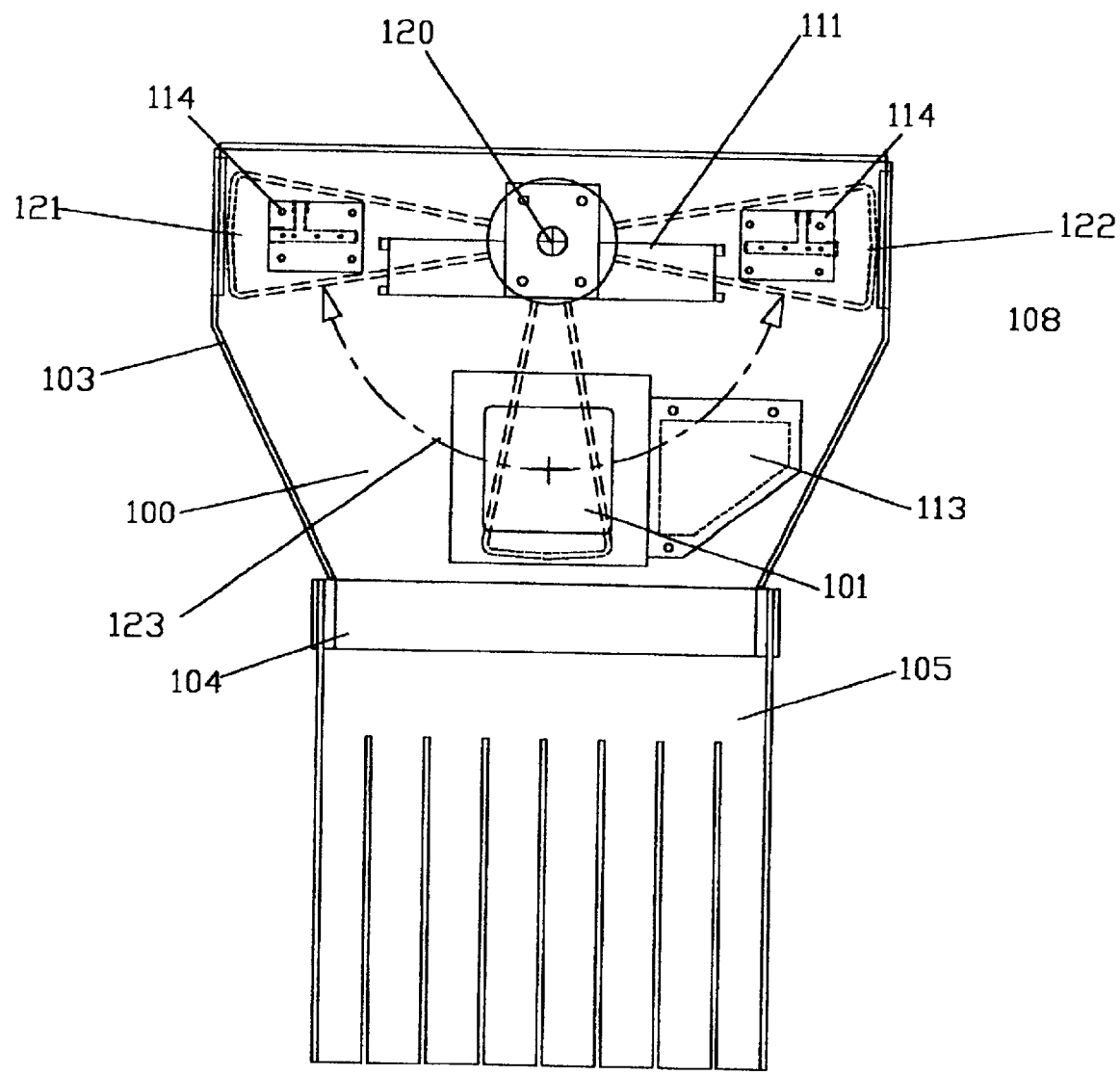
Figure 12:
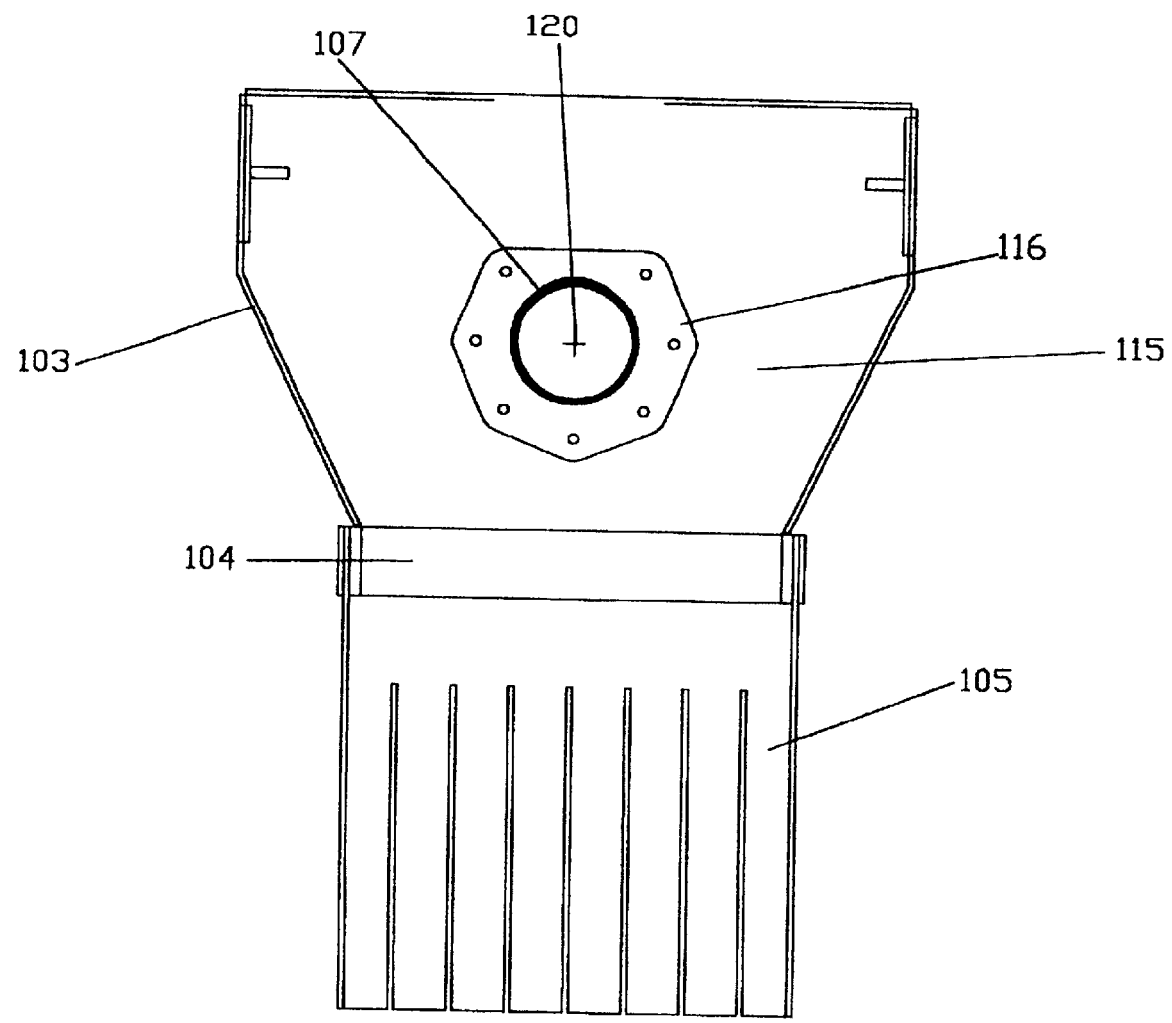
Figure 13:
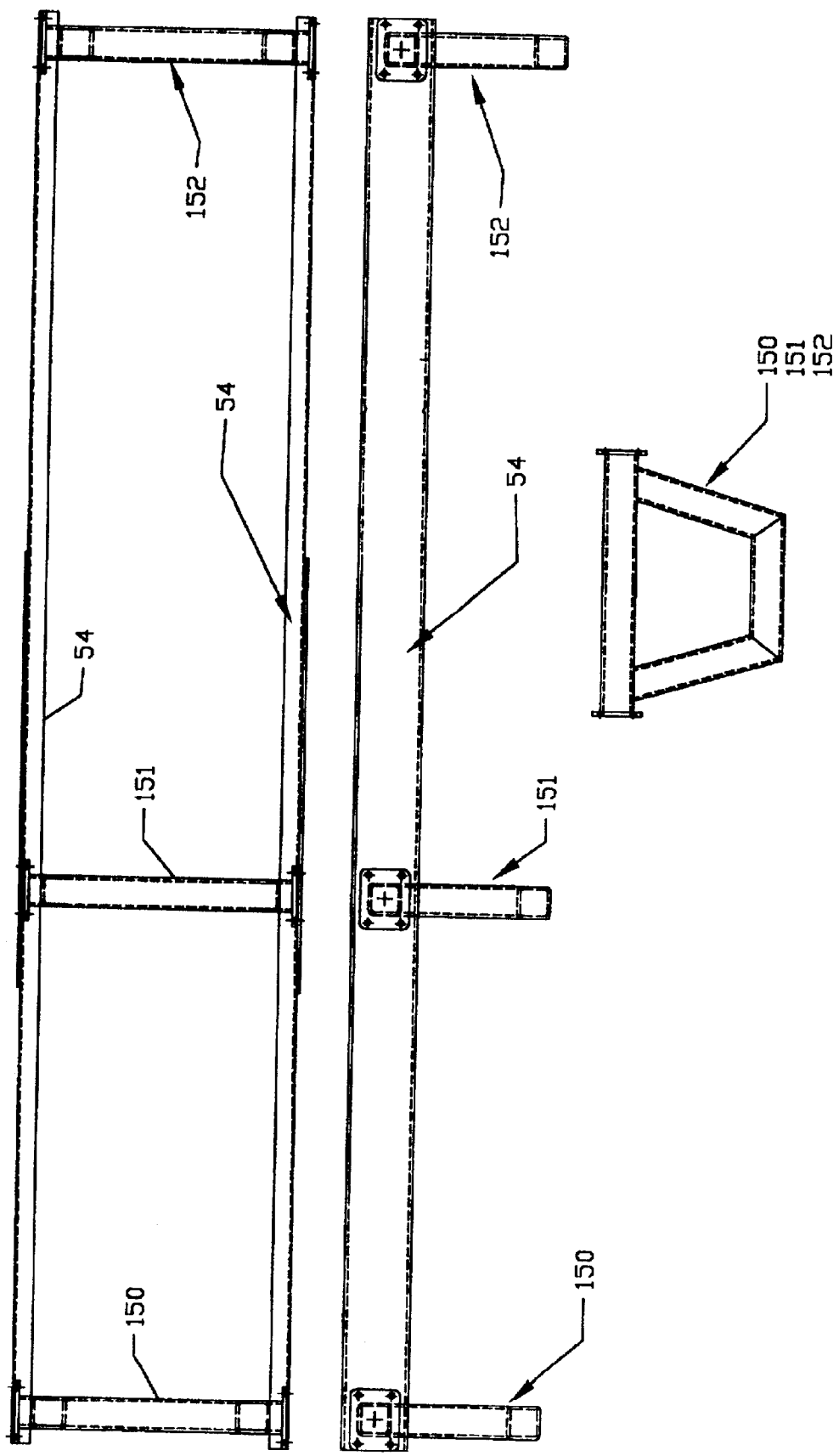
Figure 14:
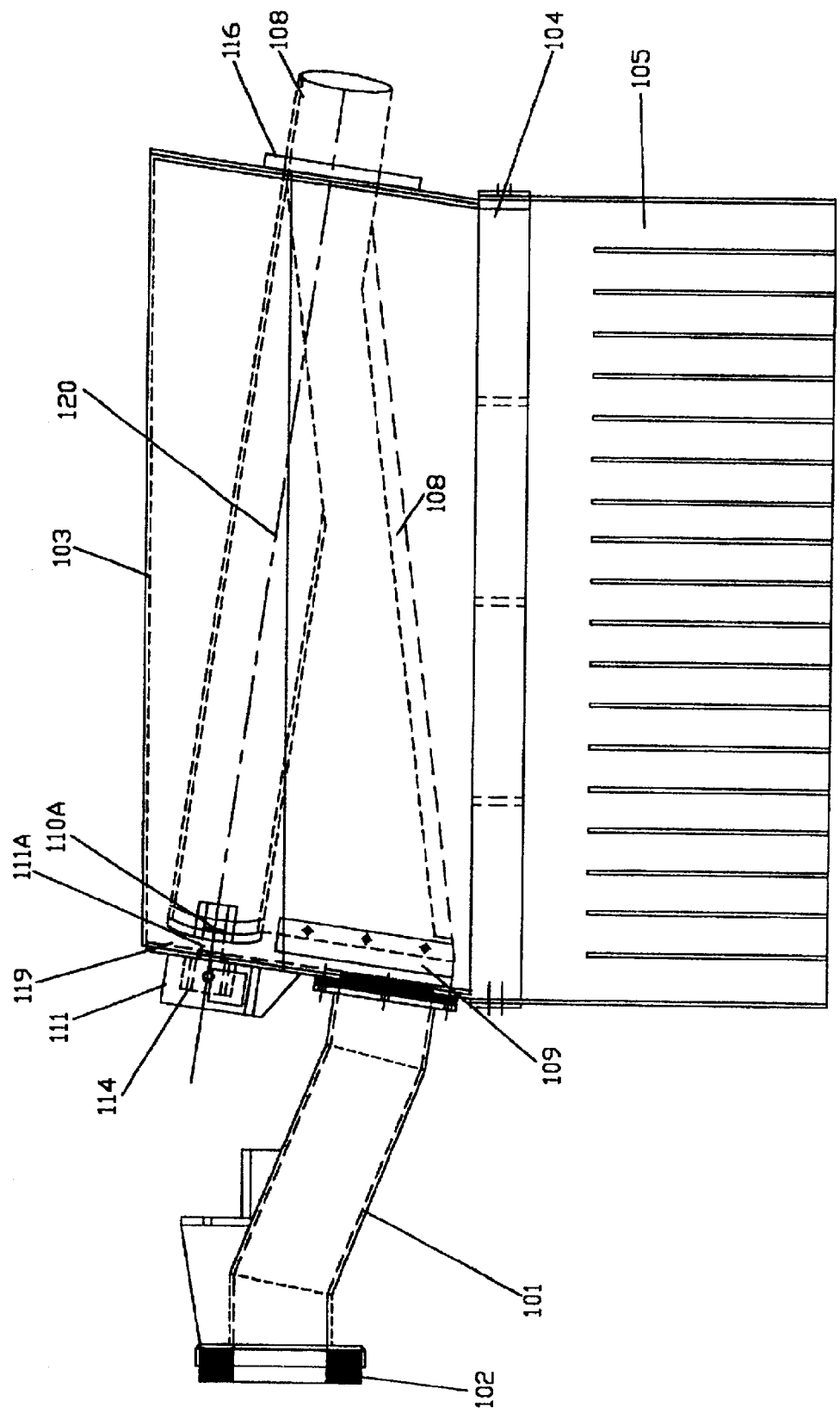
Figure 15:
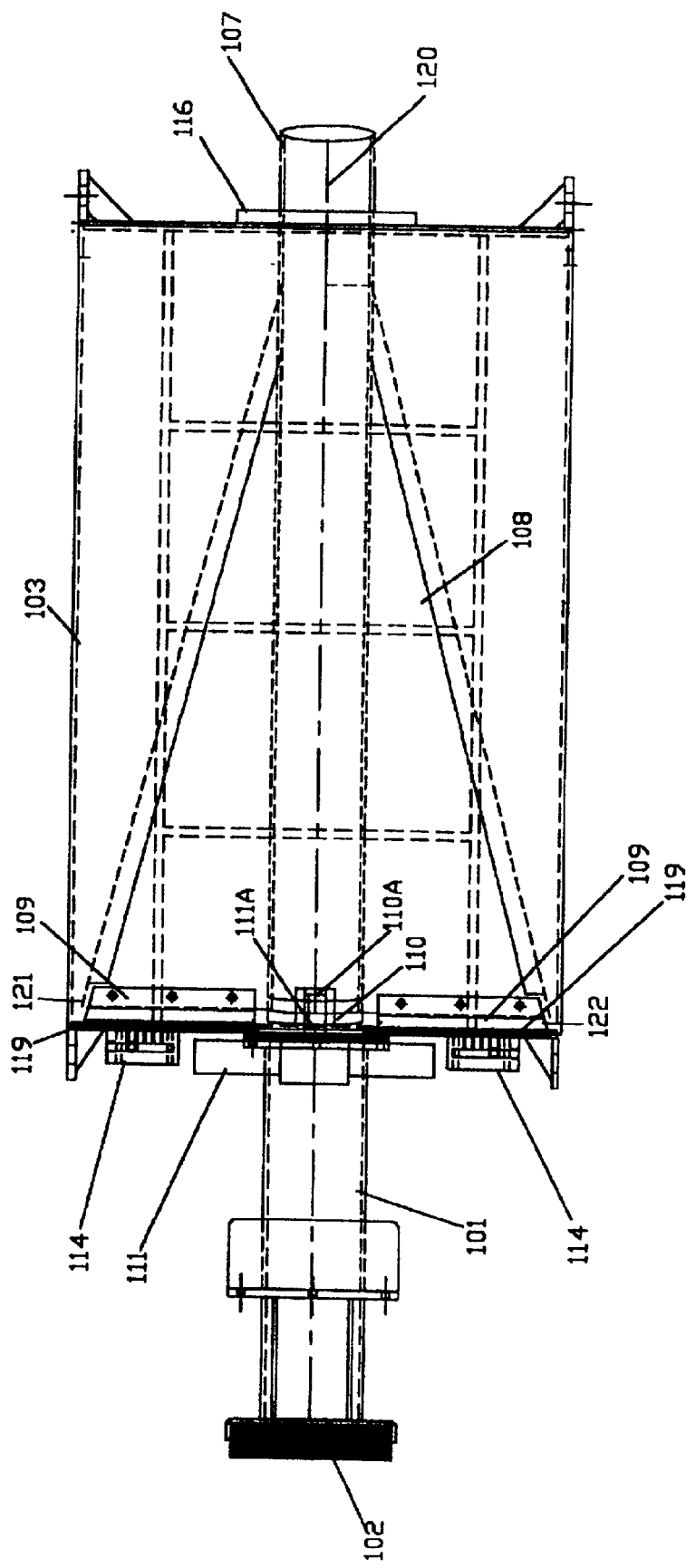
Figure 19:
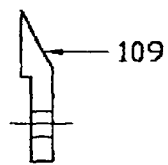
Figure 16:
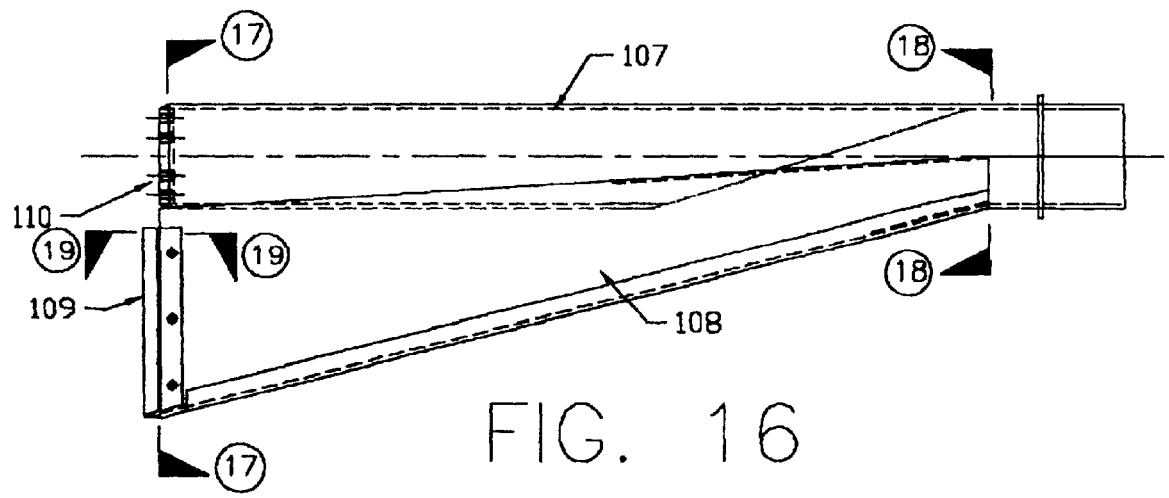
Figure 17:
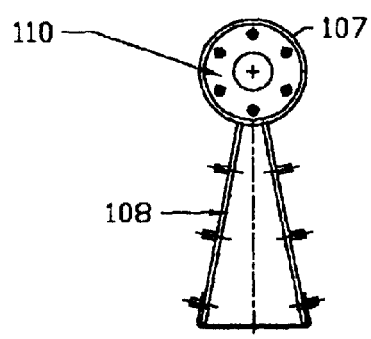
Figure 18:

As shown on FIG. 11, a cutter access/inspection door 113 is provided on the inlet end plate 100 of the enclosure 103. This door 113 allows the driller or maintenance personnel to access the cutter body 108 opening when it is stopped in position 122 for inspection and cleaning purposes. An air jet 114 is installed on this door 113 as it substitutes for the inlet end plate 100 in this position.

Figure 2:
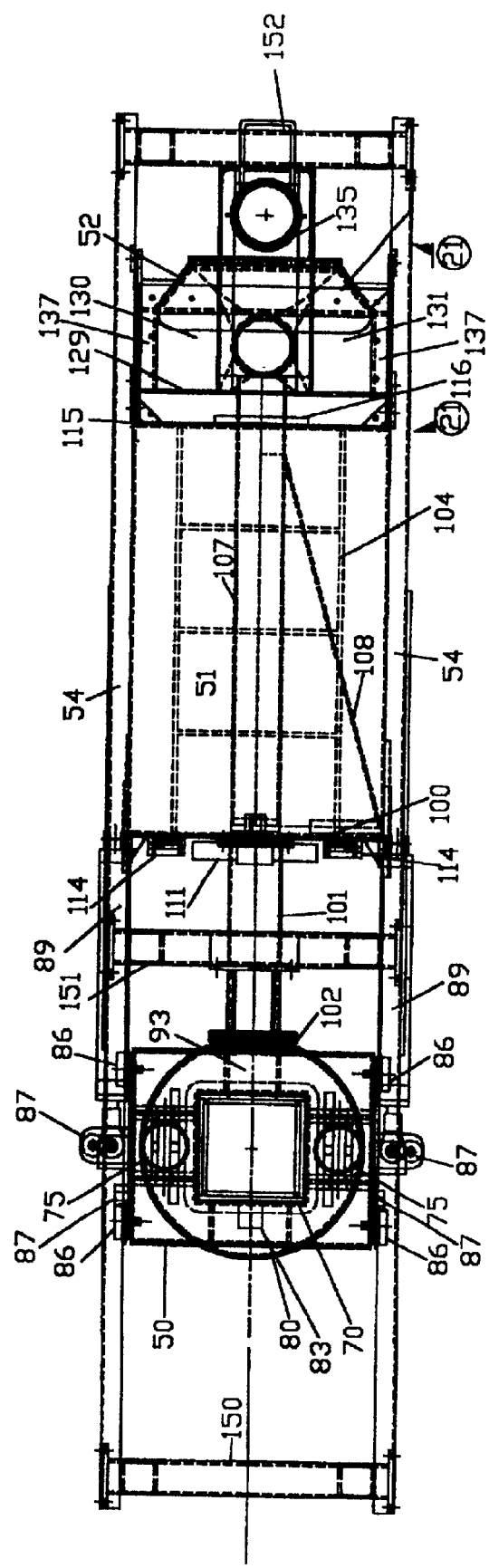

As shown on FIGS. 1 and 2 the cutter outlet pipe 107 extends through outlet end plate 115 and bushing 116 a few inches into the diffuser sample collector 52. When the air entrained sample 66 is blown through the cutter body 108 and outlet pipe 107 it enters the diffuser sample collector 52 to be collected in the bottom of the diffuser 52 for retrieval after the drill hole 63 it completed. When the sample 66 enters the chamber 127 of the diffuser 52 the entraining air must be vented off to enable the sample 66 to drop by gravity into the bottom of the sample collection chute 134. If the entraining air is not vented out, turbulence might interfere with collection on the next sample cut and fines will likely be vented out any non-sealed joint. In order to provide the venting of the entraining air, baffled vents 127 are provided near the top of the diffuser body 128.

Figure 20:
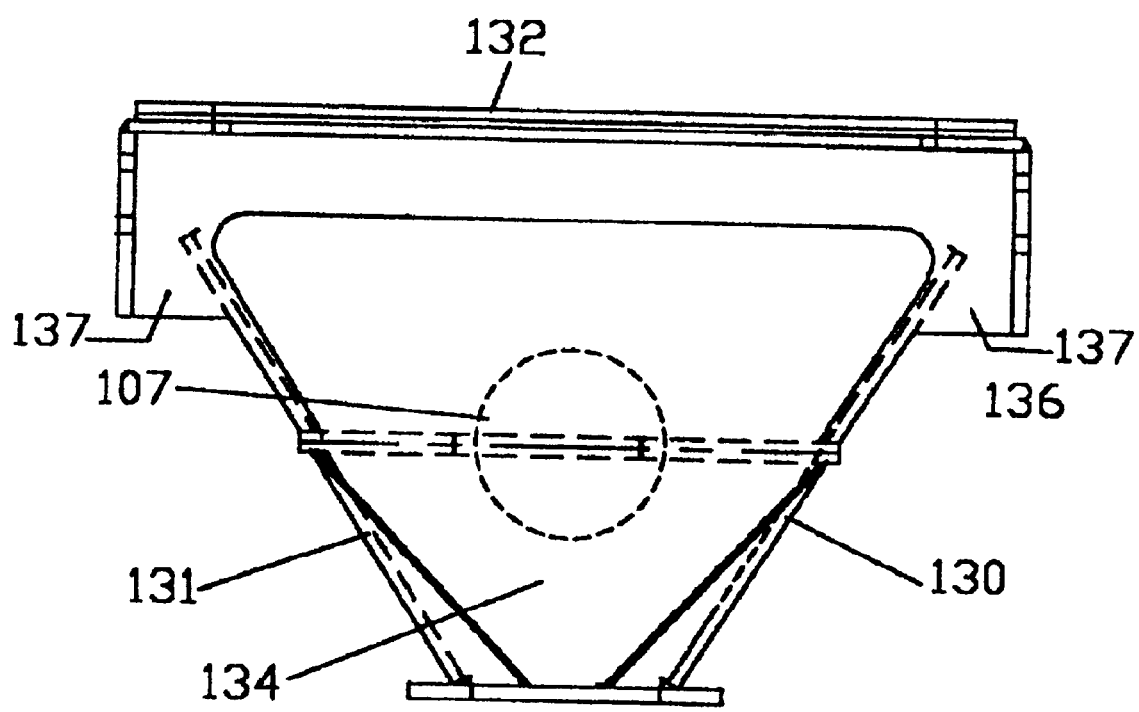
Figure 21:
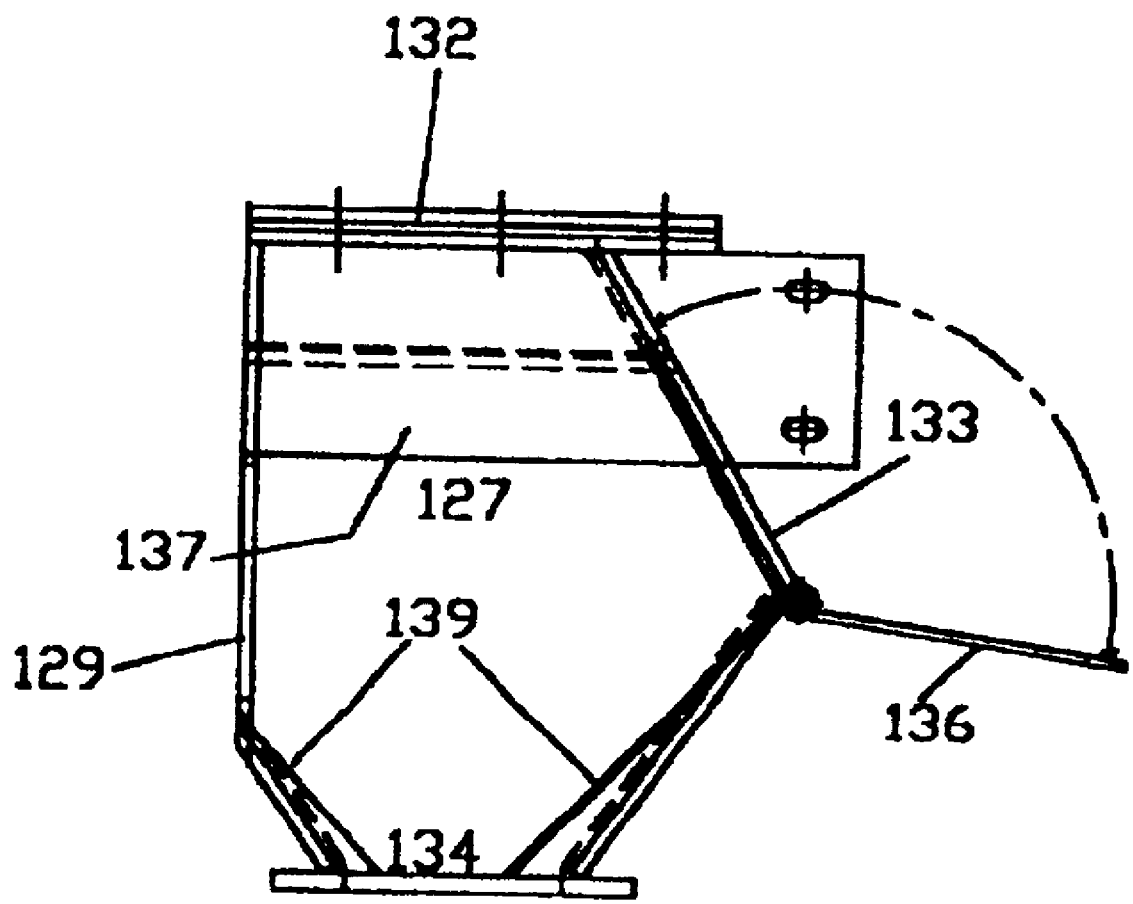
Figure 22:
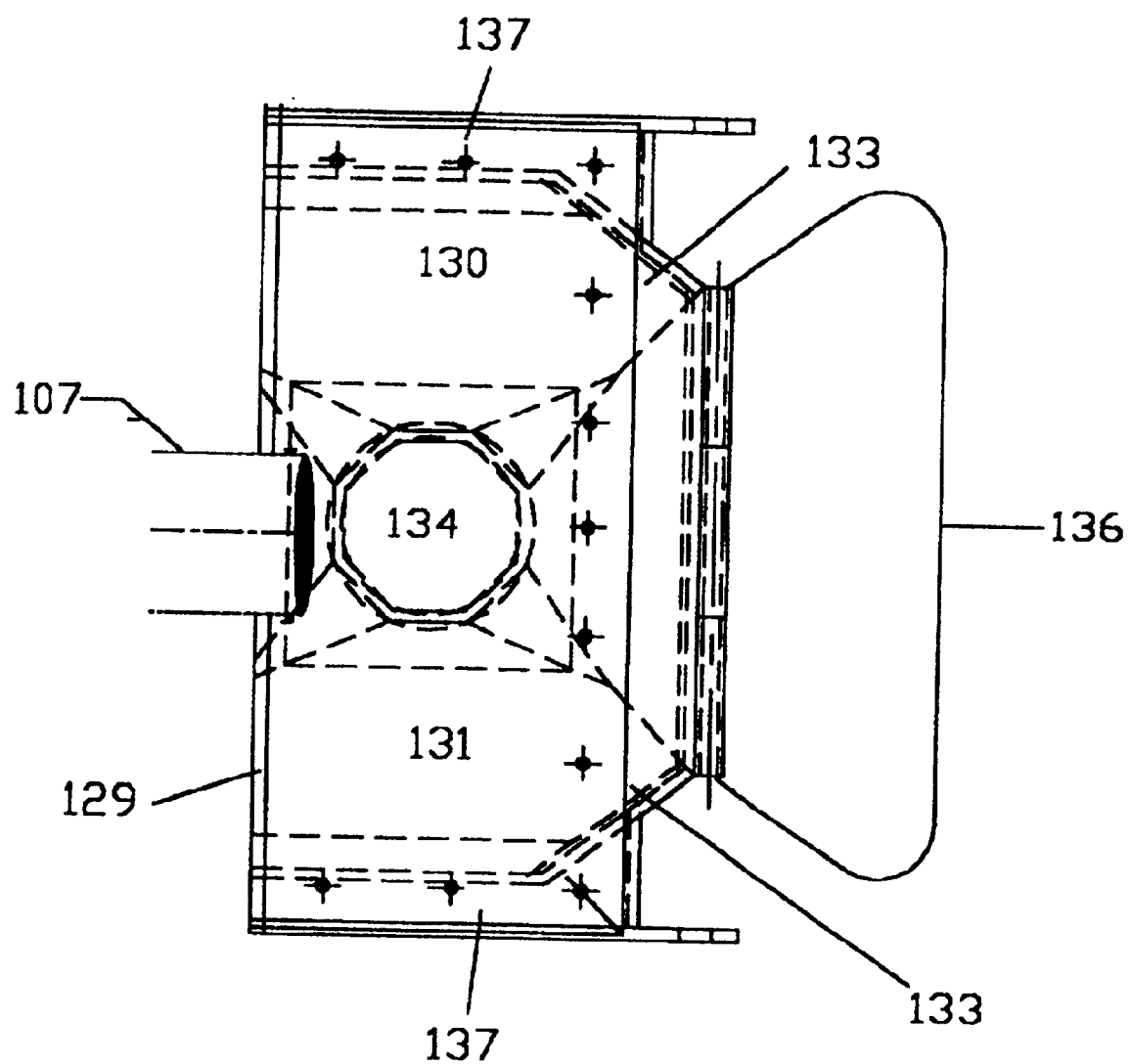
Figure 23:
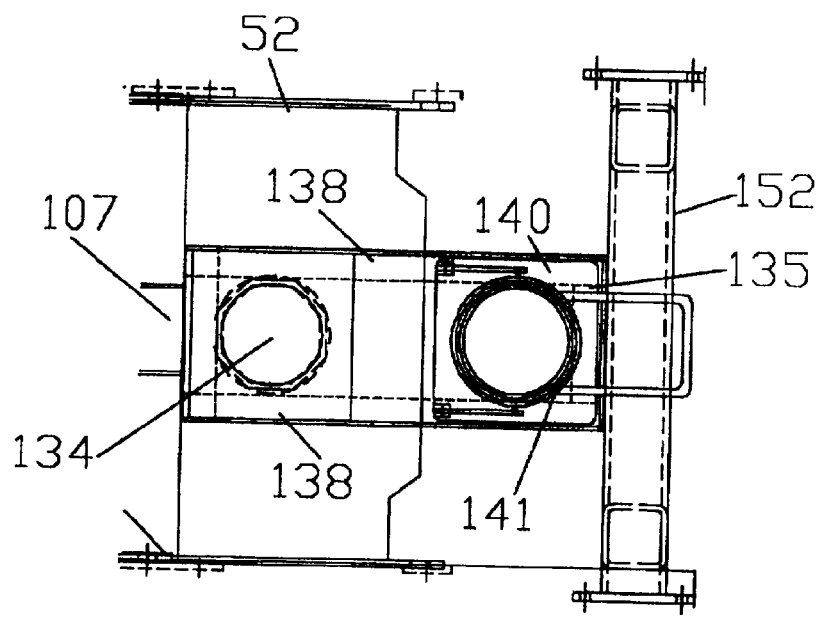
Figure 24:
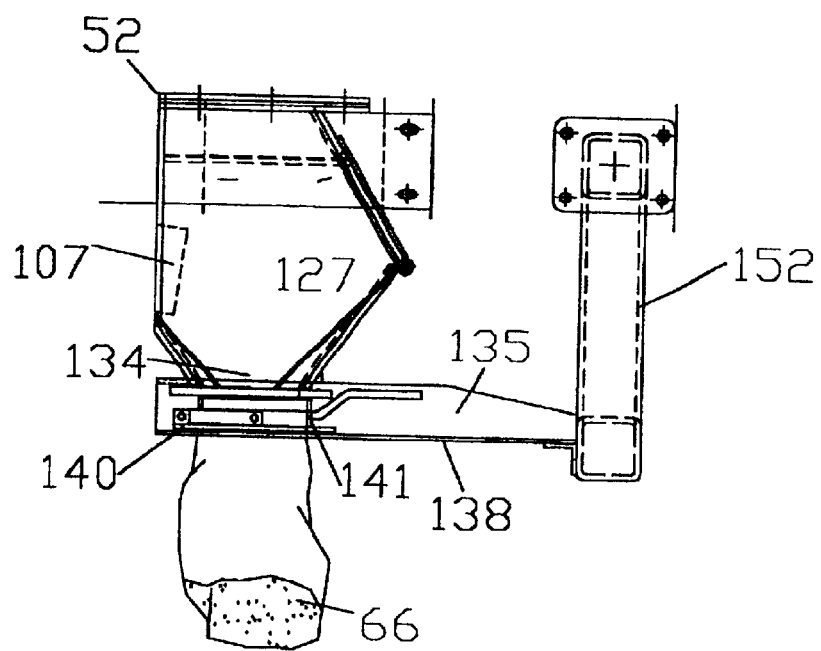

As shown in FIGS. 20, 21, and 22, diffuser 52 is comprised of a chamber 127 with an entry wall 129, side walls 130 and 131, top 132 and impact wall 133. The bottom of the chamber 127 forms a sample collection chute 134 with a sliding sample bag clamp and retrieval frame 135 as shown on FIGS. 23 and 24. The entire diffuser sample collector is secured to the channel beams 54 of the unitized frame 53 against the sampling device enclosure 103. The entry wall 129 is where the end of the sample outlet pipe 107 extends into the diffuser chamber 127. Directly below the outlet pipe 107 entry point the entry wall 129 is sloped away from the level angle of the pipe 107 and forms one side of a four-sided chute. The side walls 130 and 131 are joined to the entry wall 129 by welds at their intersections. The bottom of each side wall 130 and 131 form two more sides of the four-sided chute with the entry wall 129. Near the top of the side walls down drafting vent openings 137 are located. These are baffled to prevent direct forced air from the sample stream from entering and blowing sample cuttings 66 out of the diffuser chamber. These baffles are formed by the extension of the sloped side walls 130 and 131 above the vent openings 137 as shown on FIG. 21. The top plate 132 is fastened on to the diffuser 52 using bolts around its margins. The impact wall 133 forms the fourth wall of the four-sided sample chute and is welded to the two side walls 130 and 131. As shown FIG. 20, the top half of the impact wall 133 is an access service door 136 that allows full access to the inside of the chamber 127 and the end of the cutter outlet pipe 107. By opening this door 136, and the access door 113 on the inlet end plate 100 of the sampling device enclosure 103 with the cutter parked in position 122, clear access through the entire cutter assembly 106 is achieved. The sliding sample bag clamp and retrieval frame 135 comprised of steel angle slide rails 138 mounted on the bottom flange of sample chute 134 and attached to the frame cross support 152 supports a sliding plate 140. Sample bags are clamped to the sliding plate 140 by means of the clamp ring and handle 141. The sliding plate 140 is then pushed under the diffuser sample chute 134 for direct collection while the blast hole is being drilled. Retrieval of the sample is done by sliding the plate 140 out toward the support 152 and lifting the handle and clamp ring, thereby releasing the sample bag.

The unitized frame 53 secures all major components 50, 51, and 52 of the sampling system to the bottom of the blast hole drill rig frame as shown in FIGS. 1 and 2. The framework 53 is comprised of two heavy duty channel beams 54 that extend through the entire length of the system. These beams 54 are joined together and reinforced at both ends and where the sampler 51 and stem collector 50 meet by tubular steel bracing 150, 151 and 152. The configuration of 150, 151, and 152 performs a dual task. They not only provide connection and reinforcement between the two channels 54, they also provide collision protection for 50, 51, and 52. Terrain surfaces where the drill rigs work at an open pit mine can vary in roughness and consistency. Abrupt changes in slope near high walls and ruble piles and an occasional rock can come in contact with the equipment. These braces help keep major damage from happening to the sampling system. The stem collector 50, sampling device 51 and diffuser 52 are all fastened to the frame channels 54 which are in turn fastened to flanges that are welded on to the rig frame under the cab.

While various steps for operation of the device have just been described, changes in the steps and sequences can be made depending upon the specific installation of the apparatus. Further, some of the steps can be initiated manually while others may be initiated automatically.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

What is claimed is:

1. A sample collection device for collecting a sample of drill cuttings directly from a stream of drill cuttings from a hole having a top and being drilled with a drill having a drill pipe extending through an area from a drill deck to the top of the hole being drilled, comprising:

a stem collector positioned around the drill pipe between the top of the hole being drilled and the drill deck to entrap air-entrained drill cuttings from the hole being drilled;

a conduit extending from the stem collector to carry the air-entrained drill cuttings entrapped by the stem collector as a stream of such drill cuttings;

a sampler receiving the stream of drill cuttings directly from the conduit and periodically cutting through substantially the entire stream prior to the venting of any entraining air to obtain a sample stream which is a fraction of the stream of drill cuttings and substantially representative of the stream of drill cuttings and containing sample drill cuttings therein; and a diffuser which separates the sample drill cuttings from the air entraining the sample drill cuttings to provide a representative sample of drill cuttings from the hole being drilled.

2. A sample collection device according to claim 1, wherein the stem collector substantially seals the area around the drill pipe between the drill deck and the top of the hole being drilled.

3. A sample collection device according to claim 2, wherein the top of the hole is surrounded with ground and the stem collector includes a ground contacting end which contacts the ground surrounding the top of the hole.

4. A sample collection device according to claim 3, wherein the ground contacting end of the stem collector is forced with pressure against the ground surrounding the hole.

5. A sample collection device according to claim 4, wherein the end of the stem collector forced with pressure against the ground surrounding the hole is equipped with a two part sealing system including a toothed section and a resilient sealing ring surrounding the toothed section.

6. A sample collection device according to claim 5, additionally including hydraulic cylinders to force the ground contacting end of the stem collector against the ground with adjustable force to insure effective contact without causing damage to the stem collector base.

7. A sample collection device according to claim 5, additionally including linear actuators to force the ground contacting end of the stem collector against the ground with adjustable force to insure effective contact without causing damage to the stem collector base.

8. A sample collection device according to claim 1, wherein the sampler includes a cutter that periodically moves through the stream of drill cuttings to obtain the sample stream in a manner wherein all particles in the entrained cutting stream have a substantially equal opportunity of becoming a part of the sample taken.

9. A sample collection device according to claim 8, wherein the cutter rotates about a shaft from one parked position to a second parked position and passes through the stream of drill cuttings therebetween.

10. A sample collection device according to claim 9, wherein the cutter remains in the parked positions for a pre-set time period and the pre-set time period determines the fraction of the stream of drill cuttings in the sample stream.

11. A sample collection device according to claim 8, wherein the sampler is a rotary cutter sampler moving in a limited controlled arc in both directions between parked positions.

12. A sample collection device according to claim 8, wherein the cutter rotates about a shaft from one parked position to a second parked position and passes through the stream of drill cuttings therebetween and wherein cuttings not becoming part of the sample stream drop out under the sampler.

13. A sample collection device according to claim 8, wherein the conduit extending from the stem collector to carry the air-entrained drill cuttings includes a horizontal portion and wherein the cutter rotates about a shaft from one parked position to a second parked position and passes through the horizontal stream of drill cuttings therebetween.

14. A sample collection device for collecting a sample of drill cuttings from a stream of drill cuttings from a hole in the ground having a top surrounded by ground and being drilled with a drill having a drill pipe extending through an area from a drill deck to the top of the hole being drilled, comprising:

a stem collector positioned around the drill pipe between the top of the hole being drilled and the drill deck and having a ground contacting end adapted to contact the ground surrounding the top of the hole so that the stem collector substantially seals the area around the drill pipe between the drill deck and the top of the hole being drilled to entrap air-entrained drill cuttings from the hole being drilled;

means chosen from the group consisting of hydraulic cylinders and linear actuators to force the ground contacting end of the stem collector against the ground surrounding the hole;

a conduit extending from the stem collector to carry the air-entrained drill cuttings entrapped by the stem collector as a stream of such drill cuttings;

a sampler receiving the stream of drill cuttings from the conduit and cutting such stream to obtain a sample stream which is a fraction of the stream of drill cuttings and substantially representative of the stream of drill cuttings and containing sample drill cuttings therein; and a diffuser which separates the sample drill cuttings from the air entraining the sample drill cuttings to provide a representative sample of drill cuttings from the hole being drilled.

15. A sample collection device for collecting a sample of drill cuttings from a stream of drill cuttings from a hole in the ground having a top surrounded by ground and being drilled with a drill having a drill pipe extending through an area from a drill deck to the top of the hole being drilled, comprising:

a stem collector positioned around the drill pipe between the top of the hole being drilled and the drill deck and having a ground contacting end adapted to contact the ground surrounding the top of the hole so that the stem collector substantially seals the area around the drill pipe between the drill deck and the top of the hole being drilled to entrap air-entrained drill cuttings from the hole being drilled;

means to force the ground contacting end of the stem collector against the ground surrounding the hole;

a conduit extending from the stem collector to carry the air-entrained drill cuttings entrapped by the stem collector as a stream of such drill cuttings;

a sampler receiving the stream of drill cuttings from the conduit and cutting such stream to obtain a sample stream which is a fraction of the stream of drill cuttings and substantially representative of the stream of drill cuttings and containing sample drill cuttings therein; and a diffuser which separates the sample drill cuttings from the air entraining the sample drill cuttings to provide a representative sample of drill cuttings from the hole being drilled; and wherein the drill deck is part of a movable drill rig and the drill stem can be retracted from the area between the drill deck and the top of the hole being drilled to allow travel of the drill rig, additionally including wheels to allow the stem collector to be rolled horizontally with respect to the alignment of the drill stem to a travel position to allow travel of the drill rig.

16. A sample collection device according to claim 15, additionally including means connected to the mounting frame and the stem collector to move the stem collector with respect to the alignment of the drill stem.

17. A sample collection device according to claim 16, wherein the sampler includes a cutter that periodically moves through the stream of drill cuttings to obtain the sample stream.

18. A sample collection device according to claim 17, wherein the cutter rotates about a shaft from one parked position to a second parked position and passes through the stream of drill cuttings therebetween.

19. A sample collection device according to claim 18, wherein the cutter remains in the parked positions for a pre-set time period and the pre-set time period determines the fraction of the stream of drill cuttings in the sample stream.

20. A sample collection device according to claim 19, wherein the sampler is a rotary cutter sampler.

21. A sample collection device according to claim 20, wherein the diffuser includes baffles to slow the flow of entraining air to thereby allow the sample drill cuttings to separate by gravity from the entraining air.

22. A sample collection device according to claim 21, additionally including a collection chamber for collecting the sample drill cuttings therein.

23. A sample collection device according to claim 22, additionally including a sample bag clamp and retrieval mechanism to allow the collected sample to be transferred from the diffuser and transported away from the drill rig.

24. A sample collection device according to claim 16, wherein the means connected to the mounting frame and the stem collector to move the stem collector with respect to the alignment of the drill stem is chosen from the group consisting of hydraulic cylinders and linear actuators.

* * * * *